(12) United States Patent
Abken et al.

(10) Patent No.: US 10,865,243 B2
(45) Date of Patent: Dec. 15, 2020

(54) CHIMERIC ANTIGEN RECEPTOR AND ITS USE

(71) Applicants: Hinrich Abken, Cologne (DE); Andreas Hombach, Cologne (DE)

(72) Inventors: Hinrich Abken, Cologne (DE); Andreas Hombach, Cologne (DE)

(*) Notice: Subject to any disclaimer, the term of this patent is extended or adjusted under 35 U.S.C. 154(b) by 0 days.

(21) Appl. No.: 15/325,638

(22) PCT Filed: Jul. 16, 2015

(86) PCT No.: PCT/EP2015/066252
§ 371 (c)(1),
(2) Date: Jan. 11, 2017

(87) PCT Pub. No.: WO2016/008973
PCT Pub. Date: Jan. 21, 2016

(65) Prior Publication Data
US 2017/0145095 A1    May 25, 2017

(30) Foreign Application Priority Data
Jul. 16, 2014   (EP) .................... 14177278

(51) Int. Cl.
| | |
|---|---|
| *A61K 35/17* | (2015.01) |
| *C12N 15/62* | (2006.01) |
| *C12N 15/63* | (2006.01) |
| *A61K 39/00* | (2006.01) |
| *C07K 16/28* | (2006.01) |
| *C07K 14/725* | (2006.01) |
| *C07K 16/30* | (2006.01) |
| *C07K 14/705* | (2006.01) |
| *C07K 14/735* | (2006.01) |

(52) U.S. Cl.
CPC ...... *C07K 16/2803* (2013.01); *C07K 14/7051* (2013.01); *C07K 14/70521* (2013.01); *C07K 14/70535* (2013.01); *C07K 16/2878* (2013.01); *C07K 16/3007* (2013.01); *A61K 2039/505* (2013.01); *C07K 2317/24* (2013.01); *C07K 2317/622* (2013.01); *C07K 2319/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 2013/0011386 A1* | 1/2013 | Brezski | C07K 16/00 424/130.1 |
| 2013/0280220 A1* | 10/2013 | Ahmed | C12N 15/85 424/93.21 |

OTHER PUBLICATIONS

Nogales et al., Germ Cell Tumors of the Ovary an Update. Arch Pathol Lab Med—vol. 138, Mar. 2014 pp. 351-362.*
Savoldo et al., 2007 Epstein Barr virus—specific cytotoxic T lymphocytes expressing the anti-CD30 artificial chimeric T-cell receptor for immunotherapy of Hodgkin disease Blood pp. 2620-2630.*
Hombach et al Gene Therapy (2010) 17, 1206-1213 Adoptive immunotherapy with genetically engineered T cells: modification of the IgG1 Fc 'spacer' domain in the extracellular moiety of chimeric antigen receptors.*
Paul, Fundamental Immunology, 3rd Edition, 1993, pp. 292-295.*
Rudikoff et al., Proc. Natl. Acad. Sci. USA, 79(6):1979-1983, Mar. 1982.*
Hombach et al., Cancer Research 58. 1116-1119. Mar. 15, 1998].*
Chmielewski M. et al: "Antigen-specific T-cell activation independently of the MHC: chimeric antigen receptor—redirected T cells", Frontiers in Immunology, vol. 4, article 371, pp. 1-7, Nov. 11, 2013.
Chmielewski M. et al: "Of Cars and Trucks: chimeric antigen receptor (CAR) T cells engineered with an inducible cytokine to modulate the tumor stroma", John Wiley & Sons Ltd. Immunological Reviews, vol. 257, pp. 83-90, 2014.
Bridgeman J. et al: Building Better Chimeric Antigen Receptors for Adoptive T Cell Therapy, Current Gene Therapy, Bentham Science Publishers Ltd., vol. 10, pp. 77-90, 2010.

(Continued)

*Primary Examiner* — Maria G Leavitt
(74) *Attorney, Agent, or Firm* — W & C IP

(57) ABSTRACT

In a first aspect, the present invention relates to a recombinant polypeptide containing a domain comprising at least two antibody units whereby the first antibody unit is an anti-CD30 single chain antibody unit while the second antibody unit is a antibody unit being specific for an antigen present on the surface of a predetermined target cell. In particular, the present invention relates to a recombinant polypeptide containing at least the following domains starting from the N-terminus to the C-terminus: a first domain containing an anti-CD30 single chain antibody unit, in particular, HRS3 scFv of SEQ ID No. 2 or homologs thereof having at least 70% identity with SEQ ID No. 2 binding specifically to CD30, and an antibody unit said antibody unit being specific for an antigen present on the surface of a predetermined target cell, in particular, being specific for a tumor-associated antigen; optionally a spacer domain; a trans-membrane domain; and a cytoplasmatic signalling domain. In a further aspect, the present invention relates to a nucleic acid molecule encoding the polypeptide according to the present invention, as well as vectors and cells containing the same. Moreover, lymphocytes are provided, in particular T-cells like CD8$^+$ or a CD4$^+$ T-cell expressing on its surface chimeric antigen receptors containing an anti-CD30 single chain antibody unit and an antibody unit whereby said antibody unit being specific for an antigen present on the surface of a predetermined target cell. Immune cells modified with the polypeptide show improved functions, in particular in the treatment of cancer, in particular CD30$^-$ cancer. That is, the cells are for use in adapted cell therapy for treating cancer in a subject in need thereof.

21 Claims, 6 Drawing Sheets
Specification includes a Sequence Listing.

(56) References Cited

OTHER PUBLICATIONS

Gilham D. et al: CAR-T cells and solid tumors: tuning T cells to challenge an inveterate foe, Trends in Molecular Medicine, vol. 18, No. 7, pp. 377-384, Jul. 2012.

Grada Z. et al: "TanCAR: A Novel Bispecific Chimeric Antigen Recpetor for Cancer Immunotherapy", Molecular Therapy-Nucleic Acids, pp. 1-11, Jul. 9, 2013.

Hombach A. et al: "The Weal and Woe of Constimulation in the Adoptive Therapy of Cancer with Chimeric Antigen Receptor (CAR)-Redirected T Cells", Current Molecular Medicine, Bentham Science Publishers, vol. 13, pp. 1-10, 2013.

Hombach A. et al: "Adoptive immunotherapy with genetically engineered T cells: modification of the IgG1 Fc spacer' domain in the extracellular moiety of chimeric antigen receptors avoids 'off-target' activation and unitended initiation of an innate immune response", Gene Therapy, vol. 17, pp. 1206-1213, 2010.

Hombach A. et al: "An Anti-CD30 Chimeric Receptor That Mediates CD3-zeta-independent T-Cell Activation against Hodgkin's lymphoma Cells in the Presence of Soluble CD30", American Association for Cancer Research, pp. 1116-1119, Mar. 15, 1998.

Kloss C. et al: "Combinatorial antigen recognition with balanced signaling promotes selective tumor eradication by engineered T Cells", Nature Biotechnology, vol. 31, No. 1, pp. 71-76, Jan. 2013.

Kofler D. et al: "CD28 Costimulation Impair the Efficacy of a Redirected T-cell Antitumor Attack in the Presence of Regulatory T cells Which Can Be Overcome by Preventing Lck Activation", The American Society of Gene & Cell Therapy, vol. 19, No. 4, pp. 760-767, Apr. 2011.

Melenhorst J. et al: "Innovation and opportunity for chimeric antigen receptor targeted T cells", International Society For Cellular Therapy, vol. 15, pp. 1046-1053, Feb. 19, 2013.

Wilkie S. et al: "Dual Targeting of ErbB2 and MUC1 in Breast Cancer Using Chimeric Antigen Receptors Engineered to Provide Complementary Signaling", vol. 32, pp. 1059-1070, Apr. 17, 2012.

Di Stasi et al., "T lymphocytes coexpressing CCR4 and a chimeric antigen receptor targeting CD30 have improved homing and anti-tumor activity in a Hodgkin tumor model", BLOOD, Jun. 18, 2009, vol. 113, No. 25.

* cited by examiner

A

946: anti-CEA CAR

1457: anti-CD30/CEA CAR

1576: anti-CD25/CEA CAR

B

A

1587: anti-CD30/Muc1 CAR

1650: anti-CD30/TAG-72 CAR

B

SEQUENCE LISTING

<160> NUMBER OF SEQ ID NOS: 22

<210> SEQ ID NO 1
<211> LENGTH: 756
<212> TYPE: DNA
<213> ORGANISM: human
<220> FEATURE:
<221> NAME/KEY: CDS
<222> LOCATION: (1)..(756)

<400> SEQUENCE: 1 aga atg gcc cag gtg caa ctg cag cag tca ggg gct gag ctg gct aga    48

```
                Arg Met Ala Gln Val Gln Leu Gln Gln Ser Gly Ala Glu Leu Ala Arg
                1               5                   10                  15 cct ggg gct tca gtg aag atg tcc tgc aag gct tct ggc tac acc ttt         96
Pro Gly Ala Ser Val Lys Met Ser Cys Lys Ala Ser Gly Tyr Thr Phe
                20                  25                  30 act acc tac aca ata cac tgg gta aga cgg agg cct gga cac gat ctg         144
Thr Thr Tyr Thr Ile His Trp Val Arg Arg Arg Pro Gly His Asp Leu
            35                  40                  45 gaa tgg att gga tac att aat cct agc agt gga tgt tct gac tac aat         192
Glu Trp Ile Gly Tyr Ile Asn Pro Ser Ser Gly Cys Ser Asp Tyr Asn
    50                  55                  60 caa aac ttc aag ggc aag acc aca ttg act gca gac aag tcc tcc aac         240
Gln Asn Phe Lys Gly Lys Thr Thr Leu Thr Ala Asp Lys Ser Ser Asn
65                  70                  75                  80 aca gcc tac atg caa ctg aac agc ctg aca tct gag gac tct gcg gtc         288
Thr Ala Tyr Met Gln Leu Asn Ser Leu Thr Ser Glu Asp Ser Ala Val
                85                  90                  95 tat tac tgt gca aga aga gcg gac tat ggt aac tac gaa tat acc tgg         336
Tyr Tyr Cys Ala Arg Arg Ala Asp Tyr Gly Asn Tyr Glu Tyr Thr Trp
            100                 105                 110 ttt gct tac tgg ggc caa ggg acc acg gtc acc gtc tcc tca agt gga        384
Phe Ala Tyr Trp Gly Gln Gly Thr Thr Val Thr Val Ser Ser Ser Gly
        115                 120                 125 ggc ggt tca ggt gga ggt ggc tct ggc ggt ggc gga tcg gtc atc gag         432
Gly Gly Ser Gly Gly Gly Gly Ser Gly Gly Gly Gly Ser Val Ile Glu
130                 135                 140 ctc act cag tct cca aaa ttc atg tcc aca tca gta gga gac agg gtc         480
Leu Thr Gln Ser Pro Lys Phe Met Ser Thr Ser Val Gly Asp Arg Val
145                 150                 155                 160 aac gtc acc tac aag gcc agt cag aat gtg ggt act aat gta gcc tgg         528
Asn Val Thr Tyr Lys Ala Ser Gln Asn Val Gly Thr Asn Val Ala Trp
                165                 170                 175 ttt caa caa aaa cca ggg caa tct cct aaa gtt ctg att tac tcg gca         576
Phe Gln Gln Lys Pro Gly Gln Ser Pro Lys Val Leu Ile Tyr Ser Ala
            180                 185                 190 tct tac cga tac agt gga gtc cct gat cgc ttc aca ggc agt gga tct         624
Ser Tyr Arg Tyr Ser Gly Val Pro Asp Arg Phe Thr Gly Ser Gly Ser
        195                 200                 205 gga aca gat ttc act ctc acc atc agc aat gtg cag tct gaa gac ttg         672
Gly Thr Asp Phe Thr Leu Thr Ile Ser Asn Val Gln Ser Glu Asp Leu
    210                 215                 220 gca gag tat ttc tgt cag caa tat cac acc tat cct ctc acg ttc gga         720
Ala Glu Tyr Phe Cys Gln Gln Tyr His Thr Tyr Pro Leu Thr Phe Gly
225                 230                 235                 240 ggg ggc acc aag ctg gaa atc aaa cgg tca gat ccc                         756
Gly Gly Thr Lys Leu Glu Ile Lys Arg Ser Asp Pro
                245                 250

<210> SEQ ID NO 2
<211> LENGTH: 252
<212> TYPE: PRT
<213> ORGANISM: human

<400> SEQUENCE: 2

Arg Met Ala Gln Val Gln Leu Gln Gln Ser Gly Ala Glu Leu Ala Arg
1               5                   10                  15

Pro Gly Ala Ser Val Lys Met Ser Cys Lys Ala Ser Gly Tyr Thr Phe
                20                  25                  30

Thr Thr Tyr Thr Ile His Trp Val Arg Arg Arg Pro Gly His Asp Leu
            35                  40                  45
```

```
Glu Trp Ile Gly Tyr Ile Asn Pro Ser Ser Gly Cys Ser Asp Tyr Asn
        50                  55                  60

Gln Asn Phe Lys Gly Lys Thr Thr Leu Thr Ala Asp Lys Ser Ser Asn
65                  70                  75                  80

Thr Ala Tyr Met Gln Leu Asn Ser Leu Thr Ser Glu Asp Ser Ala Val
                85                  90                  95

Tyr Tyr Cys Ala Arg Arg Ala Asp Tyr Gly Asn Tyr Glu Tyr Thr Trp
            100                 105                 110

Phe Ala Tyr Trp Gly Gln Gly Thr Thr Val Thr Val Ser Ser Ser Gly
        115                 120                 125

Gly Gly Ser Gly Gly Gly Ser Gly Gly Gly Ser Val Ile Glu
        130                 135                 140

Leu Thr Gln Ser Pro Lys Phe Met Ser Thr Ser Val Gly Asp Arg Val
145                 150                 155                 160

Asn Val Thr Tyr Lys Ala Ser Gln Asn Val Gly Thr Asn Val Ala Trp
                165                 170                 175

Phe Gln Gln Lys Pro Gly Gln Ser Pro Lys Val Leu Ile Tyr Ser Ala
            180                 185                 190

Ser Tyr Arg Tyr Ser Gly Val Pro Asp Arg Phe Thr Gly Ser Gly Ser
        195                 200                 205

Gly Thr Asp Phe Thr Leu Thr Ile Ser Asn Val Gln Ser Glu Asp Leu
    210                 215                 220

Ala Glu Tyr Phe Cys Gln Gln Tyr His Thr Tyr Pro Leu Thr Phe Gly
225                 230                 235                 240

Gly Gly Thr Lys Leu Glu Ile Lys Arg Ser Asp Pro
                245                 250
```

```
<210> SEQ ID NO 3
<211> LENGTH: 734
<212> TYPE: DNA
<213> ORGANISM: artificial sequence
<220> FEATURE:
<223> OTHER INFORMATION: synthetic peptide
<220> FEATURE:
<221> NAME/KEY: CDS
<222> LOCATION: (1)..(732)

<400> SEQUENCE: 3
```

```
ggt gtc cac tcc cag gtc caa ctg cag gag tca ggt cca ggt ctt gtg     48
Gly Val His Ser Gln Val Gln Leu Gln Glu Ser Gly Pro Gly Leu Val
1               5                   10                  15 aga cct agc cag acc ctg agc ctg acc tgc acc gtg tct ggc ttc acc     96
Arg Pro Ser Gln Thr Leu Ser Leu Thr Cys Thr Val Ser Gly Phe Thr
            20                  25                  30 atc agc agt ggt tat agc tgg cac tgg gtg aga cag cca cct gga cga    144
Ile Ser Ser Gly Tyr Ser Trp His Trp Val Arg Gln Pro Pro Gly Arg
        35                  40                  45 ggt ctt gag tgg att gga tac ata cag tac agt ggt atc act aac tac    192
Gly Leu Glu Trp Ile Gly Tyr Ile Gln Tyr Ser Gly Ile Thr Asn Tyr
    50                  55                  60 aac ccc tct ctc aaa agt aga gtg aca atg ctg gta gac acc agc aag    240
Asn Pro Ser Leu Lys Ser Arg Val Thr Met Leu Val Asp Thr Ser Lys
65                  70                  75                  80 aac cag ttc agc ctg aga ctc agc agc gtg aca gcc gcc gac acc gcg    288
Asn Gln Phe Ser Leu Arg Leu Ser Ser Val Thr Ala Ala Asp Thr Ala
                85                  90                  95 gtc tat tat tgt gca aga gaa gac tat gat tac cac tgg tac ttc gat    336
Val Tyr Tyr Cys Ala Arg Glu Asp Tyr Asp Tyr His Trp Tyr Phe Asp
```

```
                100                 105                 110
gtc tgg ggc caa ggg acc acg gtc acc gtc tcc tca gga ggt ggt gga    384
Val Trp Gly Gln Gly Thr Thr Val Thr Val Ser Ser Gly Gly Gly
        115                 120                 125 tcg ggc ggt ggc ggg tcg ggt ggc ggc gga tct gac atc cag ctg acc    432
Ser Gly Gly Gly Gly Ser Gly Gly Gly Gly Ser Asp Ile Gln Leu Thr
    130                 135                 140 cag agc cca agc agc ctg agc gcc agc gtg ggt gac aga gtg acc atc    480
Gln Ser Pro Ser Ser Leu Ser Ala Ser Val Gly Asp Arg Val Thr Ile
145                 150                 155                 160 acc tgt agt acc agc tcg agt gta agt tac atg cac tgg tac cag cag    528
Thr Cys Ser Thr Ser Ser Ser Val Ser Tyr Met His Trp Tyr Gln Gln
                165                 170                 175 aag cca ggt aag gct cca aag ctg ctg atc tac agc aca tcc aac ctg    576
Lys Pro Gly Lys Ala Pro Lys Leu Leu Ile Tyr Ser Thr Ser Asn Leu
            180                 185                 190 gct tct ggt gtg cca agc aga ttc agc ggt agc ggt agc ggt acc gac    624
Ala Ser Gly Val Pro Ser Arg Phe Ser Gly Ser Gly Ser Gly Thr Asp
        195                 200                 205 ttc acc ttc acc atc agc agc ctc cag cca gag gac atc gcc acc tac    672
Phe Thr Phe Thr Ile Ser Ser Leu Gln Pro Glu Asp Ile Ala Thr Tyr
    210                 215                 220 tac tgc cat cag tgg agt agt tat ccc acg ttc ggc caa ggg acc aag    720
Tyr Cys His Gln Trp Ser Ser Tyr Pro Thr Phe Gly Gln Gly Thr Lys
225                 230                 235                 240 gtg gag atc aaa gt                                                 734
Val Glu Ile Lys <210> SEQ ID NO 4
<211> LENGTH: 244
<212> TYPE: PRT
<213> ORGANISM: artificial sequence
<220> FEATURE:
<223> OTHER INFORMATION: Synthetic Construct

<400> SEQUENCE: 4

Gly Val His Ser Gln Val Gln Leu Gln Glu Ser Gly Pro Gly Leu Val
1               5                   10                  15

Arg Pro Ser Gln Thr Leu Ser Leu Thr Cys Thr Val Ser Gly Phe Thr
            20                  25                  30

Ile Ser Ser Gly Tyr Ser Trp His Trp Val Arg Gln Pro Pro Gly Arg
        35                  40                  45

Gly Leu Glu Trp Ile Gly Tyr Ile Gln Tyr Ser Gly Ile Thr Asn Tyr
    50                  55                  60

Asn Pro Ser Leu Lys Ser Arg Val Thr Met Leu Val Asp Thr Ser Lys
65                  70                  75                  80

Asn Gln Phe Ser Leu Arg Leu Ser Ser Val Thr Ala Ala Asp Thr Ala
                85                  90                  95

Val Tyr Tyr Cys Ala Arg Glu Asp Tyr Asp Tyr His Trp Tyr Phe Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Ser Asp Ile Gln Leu Thr
    130                 135                 140

Gln Ser Pro Ser Ser Leu Ser Ala Ser Val Gly Asp Arg Val Thr Ile
145                 150                 155                 160

Thr Cys Ser Thr Ser Ser Ser Val Ser Tyr Met His Trp Tyr Gln Gln
                165                 170                 175
```

```
Lys Pro Gly Lys Ala Pro Lys Leu Leu Ile Tyr Ser Thr Ser Asn Leu
            180                 185                 190

Ala Ser Gly Val Pro Ser Arg Phe Ser Gly Ser Gly Ser Gly Thr Asp
        195                 200                 205

Phe Thr Phe Thr Ile Ser Ser Leu Gln Pro Glu Asp Ile Ala Thr Tyr
    210                 215                 220

Tyr Cys His Gln Trp Ser Ser Tyr Pro Thr Phe Gly Gln Gly Thr Lys
225                 230                 235                 240

Val Glu Ile Lys

<210> SEQ ID NO 5
<211> LENGTH: 705
<212> TYPE: DNA
<213> ORGANISM: artificial
<220> FEATURE:
<223> OTHER INFORMATION: synthetic nucleic acid
<220> FEATURE:
<221> NAME/KEY: CDS
<222> LOCATION: (1)..(705)

<400> SEQUENCE: 5 gat ccc gcc gag ccc aaa tct cct gac aaa act cac aca tgc cca ccg      48
Asp Pro Ala Glu Pro Lys Ser Pro Asp Lys Thr His Thr Cys Pro Pro
1               5                   10                  15 tgc cca gca cct cca gtc gcg gga ccg tca gtc ttc ctc ttc ccc cca      96
Cys Pro Ala Pro Pro Val Ala Gly Pro Ser Val Phe Leu Phe Pro Pro
            20                  25                  30 aaa ccc aag gac acc ctc atg atc gcc cgg acc cct gag gtc aca tgc     144
Lys Pro Lys Asp Thr Leu Met Ile Ala Arg Thr Pro Glu Val Thr Cys
        35                  40                  45 gtg gtg gtg gac gtg agc cac gaa gac cct gag gtc aag ttc aac tgg     192
Val Val Val Asp Val Ser His Glu Asp Pro Glu Val Lys Phe Asn Trp
    50                  55                  60 tac gtg gac ggc gtg gag gtg cat aat gcc aag aca aag ccg cgg gag     240
Tyr Val Asp Gly Val Glu Val His Asn Ala Lys Thr Lys Pro Arg Glu
65                  70                  75                  80 gag cag tac aac agc acg tac cgt gtg gtc agc gtc ctc acc gtc ctg     288
Glu Gln Tyr Asn Ser Thr Tyr Arg Val Val Ser Val Leu Thr Val Leu
                85                  90                  95 cac cag gac tgg ctg aat ggc aag gag tac aag tgc aag gtc tcc aac     336
His Gln Asp Trp Leu Asn Gly Lys Glu Tyr Lys Cys Lys Val Ser Asn
            100                 105                 110 aaa gcc ctc cca gcc ccc atc gag aaa acc atc tcc aaa gcc aaa ggg     384
Lys Ala Leu Pro Ala Pro Ile Glu Lys Thr Ile Ser Lys Ala Lys Gly
        115                 120                 125 cag ccc cga gaa cca cag gtg tac acc ctg ccc cca tcc cgg gat gag     432
Gln Pro Arg Glu Pro Gln Val Tyr Thr Leu Pro Pro Ser Arg Asp Glu
    130                 135                 140 ctg acc aag aac cag gtc agc ctg acc tgc ctg gtc aaa ggc ttc tat     480
Leu Thr Lys Asn Gln Val Ser Leu Thr Cys Leu Val Lys Gly Phe Tyr
145                 150                 155                 160 ccc agc gac atc gcc gtg gag tgg gag agc aat ggg cag ccg gag aac     528
Pro Ser Asp Ile Ala Val Glu Trp Glu Ser Asn Gly Gln Pro Glu Asn
                165                 170                 175 aac tac aag acc acg cct ccc gtg ctg gac tcc gac ggc tcc ttc ttc     576
Asn Tyr Lys Thr Thr Pro Pro Val Leu Asp Ser Asp Gly Ser Phe Phe
            180                 185                 190 ctc tac agc aag ctc acc gtg gac aag agc agg tgg cag cag ggg aac     624
Leu Tyr Ser Lys Leu Thr Val Asp Lys Ser Arg Trp Gln Gln Gly Asn
        195                 200                 205
```

| | | |
|---|---|---|
| gtc ttc tca tgc tcc gtg atg cat gag gct ctg cac aac cac tac acg<br>Val Phe Ser Cys Ser Val Met His Glu Ala Leu His Asn His Tyr Thr<br>210                       215                       220 | | 672 |
| cag aag agc ctc tcc ctg tct ccg ggt aaa aaa<br>Gln Lys Ser Leu Ser Leu Ser Pro Gly Lys Lys<br>225                       230                       235 | | 705 |

<210> SEQ ID NO 6
<211> LENGTH: 235
<212> TYPE: PRT
<213> ORGANISM: artificial
<220> FEATURE:
<223> OTHER INFORMATION: Synthetic Construct

<400> SEQUENCE: 6

Asp Pro Ala Glu Pro Lys Ser Pro Asp Lys Thr His Thr Cys Pro Pro
1               5                   10                  15

Cys Pro Ala Pro Pro Val Ala Gly Pro Ser Val Phe Leu Phe Pro Pro
            20                  25                  30

Lys Pro Lys Asp Thr Leu Met Ile Ala Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Lys Lys
225                 230                 235

<210> SEQ ID NO 7
<211> LENGTH: 204
<212> TYPE: DNA
<213> ORGANISM: artificial
<220> FEATURE:
<223> OTHER INFORMATION: synthetic nucleic acid
<220> FEATURE:
<221> NAME/KEY: CDS
<222> LOCATION: (1)..(204)

<400> SEQUENCE: 7

| | |
|---|---|
| ttt tgg gtg ctg gtg gtg gtt ggt gga gtc ctg gct tgc tat agc ttg<br>Phe Trp Val Leu Val Val Val Gly Gly Val Leu Ala Cys Tyr Ser Leu | 48 |

```
1               5                   10                  15
cta gta aca gtg gcc ttt att att ttc tgg gtg agg agt aag agg agc      96
Leu Val Thr Val Ala Phe Ile Ile Phe Trp Val Arg Ser Lys Arg Ser
            20                  25                  30 agg ctc ctg cac agt gac tac atg aac atg act ccc cgc cgc ccc ggg     144
Arg Leu Leu His Ser Asp Tyr Met Asn Met Thr Pro Arg Arg Pro Gly
            35                  40                  45 ccc acc cgc aag cat tac cag gcc tat gcc gcc gca cgc gac ttc gca     192
Pro Thr Arg Lys His Tyr Gln Ala Tyr Ala Ala Ala Arg Asp Phe Ala
50                  55                  60 gcc tat cgc tcc                                                     204
Ala Tyr Arg Ser
65

<210> SEQ ID NO 8
<211> LENGTH: 68
<212> TYPE: PRT
<213> ORGANISM: artificial
<220> FEATURE:
<223> OTHER INFORMATION: Synthetic Construct

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
            35                  40                  45

Pro Thr Arg Lys His Tyr Gln Ala Tyr Ala Ala Ala Arg Asp Phe Ala
        50                  55                  60

Ala Tyr Arg Ser
65

<210> SEQ ID NO 9
<211> LENGTH: 414
<212> TYPE: DNA
<213> ORGANISM: human
<220> FEATURE:
<221> NAME/KEY: CDS
<222> LOCATION: (1)..(414)

<400> SEQUENCE: 9 gat ccc aaa ctc tgc tac ctg ctg gat gga atc ctc ttc atc tat ggt      48
Asp Pro Lys Leu Cys Tyr Leu Leu Asp Gly Ile Leu Phe Ile Tyr Gly
1               5                   10                  15 gtc att ctc act gcc ttg ttc ctg aga gtg aag ttc agc agg agc gca      96
Val Ile Leu Thr Ala Leu Phe Leu Arg Val Lys Phe Ser Arg Ser Ala
            20                  25                  30 gac gcc ccc gcg tac cag cag ggc cag aac cag ctc tat aac gag ctc     144
Asp Ala Pro Ala Tyr Gln Gln Gly Gln Asn Gln Leu Tyr Asn Glu Leu
            35                  40                  45 aat cta gga cga aga gag gag tac gat gtt ttg gac aag aga cgt ggc     192
Asn Leu Gly Arg Arg Glu Glu Tyr Asp Val Leu Asp Lys Arg Arg Gly
        50                  55                  60 cgg gac cct gag atg ggg gga aag ccg cag aga agg aag aac cct cag     240
Arg Asp Pro Glu Met Gly Gly Lys Pro Gln Arg Arg Lys Asn Pro Gln
65                  70                  75                  80 gaa ggc ctg tac aat gaa ctg cag aaa gat aag atg gcg gag gcc tac     288
Glu Gly Leu Tyr Asn Glu Leu Gln Lys Asp Lys Met Ala Glu Ala Tyr
                85                  90                  95 agt gag att ggg atg aaa ggc gag cgc cgg agg ggc aag ggg cac gat     336
```

```
Ser Glu Ile Gly Met Lys Gly Glu Arg Arg Gly Lys Gly His Asp
                100                 105                 110 ggc ctt tac cag ggt ctc agt aca gcc acc aag gac acc tac gac gcc   384
Gly Leu Tyr Gln Gly Leu Ser Thr Ala Thr Lys Asp Thr Tyr Asp Ala
            115                 120                 125 ctt cac atg cag gcc ctg ccc cct cgc taa                            414
Leu His Met Gln Ala Leu Pro Pro Arg
            130                 135

<210> SEQ ID NO 10
<211> LENGTH: 137
<212> TYPE: PRT
<213> ORGANISM: human

<400> SEQUENCE: 10

Asp Pro Lys Leu Cys Tyr Leu Leu Asp Gly Ile Leu Phe Ile Tyr Gly
1               5                   10                  15

Val Ile Leu Thr Ala Leu Phe Leu Arg Val Lys Phe Ser Arg Ser Ala
            20                  25                  30

Asp Ala Pro Ala Tyr Gln Gln Gly Gln Asn Gln Leu Tyr Asn Glu Leu
        35                  40                  45

Asn Leu Gly Arg Arg Glu Glu Tyr Asp Val Leu Asp Lys Arg Arg Gly
    50                  55                  60

Arg Asp Pro Glu Met Gly Gly Lys Pro Gln Arg Arg Lys Asn Pro Gln
65                  70                  75                  80

Glu Gly Leu Tyr Asn Glu Leu Gln Lys Asp Lys Met Ala Glu Ala Tyr
                85                  90                  95

Ser Glu Ile Gly Met Lys Gly Glu Arg Arg Gly Lys Gly His Asp
                100                 105                 110

Gly Leu Tyr Gln Gly Leu Ser Thr Ala Thr Lys Asp Thr Tyr Asp Ala
            115                 120                 125

Leu His Met Gln Ala Leu Pro Pro Arg
            130                 135

<210> SEQ ID NO 11
<211> LENGTH: 201
<212> TYPE: DNA
<213> ORGANISM: human
<220> FEATURE:
<221> NAME/KEY: CDS
<222> LOCATION: (1)..(201)

<400> SEQUENCE: 11 gat ccc aaa ctc tgc tat atc ctg gat gcc atc ctg ttt ctg tat gga   48
Asp Pro Lys Leu Cys Tyr Ile Leu Asp Ala Ile Leu Phe Leu Tyr Gly
1               5                   10                  15 att gtc ctc acc ctc ctc tac tgt cga ctg aag atc caa gtg cga aag   96
Ile Val Leu Thr Leu Leu Tyr Cys Arg Leu Lys Ile Gln Val Arg Lys
            20                  25                  30 gca gct ata acc agc tat gag aaa tca gat ggt gtt tac acg ggc ctg   144
Ala Ala Ile Thr Ser Tyr Glu Lys Ser Asp Gly Val Tyr Thr Gly Leu
        35                  40                  45 agc acc agg aac cag gag act tac gag act ctg aag cat gag aaa cca   192
Ser Thr Arg Asn Gln Glu Thr Tyr Glu Thr Leu Lys His Glu Lys Pro
    50                  55                  60 cca cag tag                                                        201
Pro Gln
65

<210> SEQ ID NO 12
```

-continued

```
<211> LENGTH: 66
<212> TYPE: PRT
<213> ORGANISM: human

<400> SEQUENCE: 12

Asp Pro Lys Leu Cys Tyr Ile Leu Asp Ala Ile Leu Phe Leu Tyr Gly
1               5                   10                  15

Ile Val Leu Thr Leu Leu Tyr Cys Arg Leu Lys Ile Gln Val Arg Lys
                20                  25                  30

Ala Ala Ile Thr Ser Tyr Glu Lys Ser Asp Gly Val Tyr Thr Gly Leu
            35                  40                  45

Ser Thr Arg Asn Gln Glu Thr Tyr Glu Thr Leu Lys His Glu Lys Pro
    50                  55                  60

Pro Gln
65

<210> SEQ ID NO 13
<211> LENGTH: 2943
<212> TYPE: DNA
<213> ORGANISM: artificial
<220> FEATURE:
<223> OTHER INFORMATION: synthetic sequence
<220> FEATURE:
<221> NAME/KEY: CDS
<222> LOCATION: (1)..(2943)

<400> SEQUENCE: 13 ctc tag act gcc atg gat ttt cag gtg cag att ttc agc ttc ctg cta    48
Leu     Thr Ala Met Asp Phe Gln Val Gln Ile Phe Ser Phe Leu Leu
1                   5                   10                  15 atc agt gcc tca gtc ata atg tct aga atg gcc cag gtg caa ctg cag    96
Ile Ser Ala Ser Val Ile Met Ser Arg Met Ala Gln Val Gln Leu Gln
                20                  25                  30 cag tca ggg gct gag ctg gct aga cct ggg gct tca gtg aag atg tcc   144
Gln Ser Gly Ala Glu Leu Ala Arg Pro Gly Ala Ser Val Lys Met Ser
            35                  40                  45 tgc aag gct tct ggc tac acc ttt act acc tac aca ata cac tgg gta   192
Cys Lys Ala Ser Gly Tyr Thr Phe Thr Thr Tyr Thr Ile His Trp Val
        50                  55                  60 aga cgg agg cct gga cac gat ctg gaa tgg att gga tac att aat cct   240
Arg Arg Arg Pro Gly His Asp Leu Glu Trp Ile Gly Tyr Ile Asn Pro
65                  70                  75 agc agt gga tgt tct gac tac aat caa aac ttc aag ggc aag acc aca   288
Ser Ser Gly Cys Ser Asp Tyr Asn Gln Asn Phe Lys Gly Lys Thr Thr
80                  85                  90                  95 ttg act gca gac aag tcc tcc aac aca gcc tac atg caa ctg aac agc   336
Leu Thr Ala Asp Lys Ser Ser Asn Thr Ala Tyr Met Gln Leu Asn Ser
                100                 105                 110 ctg aca tct gag gac tct gcg gtc tat tac tgt gca aga aga gcg gac   384
Leu Thr Ser Glu Asp Ser Ala Val Tyr Tyr Cys Ala Arg Arg Ala Asp
            115                 120                 125 tat ggt aac tac gaa tat acc tgg ttt gct tac tgg ggc caa ggg acc   432
Tyr Gly Asn Tyr Glu Tyr Thr Trp Phe Ala Tyr Trp Gly Gln Gly Thr
        130                 135                 140 acg gtc acc gtc tcc tca agt gga ggc ggt tca ggt gga ggt ggc tct   480
Thr Val Thr Val Ser Ser Ser Gly Gly Gly Ser Gly Gly Gly Gly Ser
    145                 150                 155 ggc ggt ggc gga tcg gtc atc gag ctc act cag tct cca aaa ttc atg   528
Gly Gly Gly Gly Ser Val Ile Glu Leu Thr Gln Ser Pro Lys Phe Met
160                 165                 170                 175 tcc aca tca gta gga gac agg gtc aac gtc acc tac aag gcc agt cag   576
```

```
                Ser Thr Ser Val Gly Asp Arg Val Asn Val Thr Tyr Lys Ala Ser Gln
                            180                 185                 190 aat gtg ggt act aat gta gcc tgg ttt caa caa aaa cca ggg caa tct          624
Asn Val Gly Thr Asn Val Ala Trp Phe Gln Gln Lys Pro Gly Gln Ser
            195                 200                 205 cct aaa gtt ctg att tac tcg gca tct tac cga tac agt gga gtc cct          672
Pro Lys Val Leu Ile Tyr Ser Ala Ser Tyr Arg Tyr Ser Gly Val Pro
            210                 215                 220 gat cgc ttc aca ggc agt gga tct gga aca gat ttc act ctc acc atc          720
Asp Arg Phe Thr Gly Ser Gly Ser Gly Thr Asp Phe Thr Leu Thr Ile
        225                 230                 235 agc aat gtg cag tct gaa gac ttg gca gag tat ttc tgt cag caa tat          768
Ser Asn Val Gln Ser Glu Asp Leu Ala Glu Tyr Phe Cys Gln Gln Tyr
240                 245                 250                 255 cac acc tat cct ctc acg ttc gga ggg ggc acc aag ctg gaa atc aaa          816
His Thr Tyr Pro Leu Thr Phe Gly Gly Gly Thr Lys Leu Glu Ile Lys
                260                 265                 270 cgg tca gat ccc gga ggc ggg ggt tct ggt gga ggc gga agc ggt ggc          864
Arg Ser Asp Pro Gly Gly Gly Gly Ser Gly Gly Gly Ser Gly Gly
                275                 280                 285 ggg ggt tca gga ggc ggg ggt tcc ggt ggt ggc ggc agt ggt ggt ggc          912
Gly Gly Ser Gly Gly Gly Gly Ser Gly Gly Gly Gly Ser Gly Gly Gly
            290                 295                 300 ggc agt ggt ggt ggc ggc agt ggt ggt ggc ggc agt ggt gtc cac tcc          960
Gly Ser Gly Gly Gly Gly Ser Gly Gly Gly Gly Ser Gly Val His Ser
        305                 310                 315 cag gtc caa ctg cag gag tca ggt cca ggt ctt gtg aga cct agc cag         1008
Gln Val Gln Leu Gln Glu Ser Gly Pro Gly Leu Val Arg Pro Ser Gln
320                 325                 330                 335 acc ctg agc ctg acc tgc acc gtg tct ggc ttc acc atc agc agt ggt         1056
Thr Leu Ser Leu Thr Cys Thr Val Ser Gly Phe Thr Ile Ser Ser Gly
                340                 345                 350 tat agc tgg cac tgg gtg aga cag cca cct gga cga ggt ctt gag tgg         1104
Tyr Ser Trp His Trp Val Arg Gln Pro Pro Gly Arg Gly Leu Glu Trp
                355                 360                 365 att gga tac ata cag tac agt ggt atc act aac tac aac ccc tct ctc         1152
Ile Gly Tyr Ile Gln Tyr Ser Gly Ile Thr Asn Tyr Asn Pro Ser Leu
            370                 375                 380 aaa agt aga gtg aca atg ctg gta gac acc agc aag aac cag ttc agc         1200
Lys Ser Arg Val Thr Met Leu Val Asp Thr Ser Lys Asn Gln Phe Ser
385                 390                 395 ctg aga ctc agc agc gtg aca gcc gcc gac acc gcg gtc tat tat tgt         1248
Leu Arg Leu Ser Ser Val Thr Ala Ala Asp Thr Ala Val Tyr Tyr Cys
400                 405                 410                 415 gca aga gaa gac tat gat tac cac tgg tac ttc gat gtc tgg ggc caa         1296
Ala Arg Glu Asp Tyr Asp Tyr His Trp Tyr Phe Asp Val Trp Gly Gln
                420                 425                 430 ggg acc acg gtc acc gtc tcc tca gga ggt ggt gga tcg ggc ggt ggc         1344
Gly Thr Thr Val Thr Val Ser Ser Gly Gly Gly Gly Ser Gly Gly Gly
                435                 440                 445 ggg tcg ggt ggc ggc gga tct gac atc cag ctg acc cag agc cca agc         1392
Gly Ser Gly Gly Gly Gly Ser Asp Ile Gln Leu Thr Gln Ser Pro Ser
            450                 455                 460 agc ctg agc gcc agc gtg ggt gac aga gtg acc atc acc tgt agt acc         1440
Ser Leu Ser Ala Ser Val Gly Asp Arg Val Thr Ile Thr Cys Ser Thr
        465                 470                 475 agc tcg agt gta agt tac atg cac tgg tac cag cag aag cca ggt aag         1488
Ser Ser Ser Val Ser Tyr Met His Trp Tyr Gln Gln Lys Pro Gly Lys
480                 485                 490                 495
```

```
gct cca aag ctg ctg atc tac agc aca tcc aac ctg gct tct ggt gtg      1536
Ala Pro Lys Leu Leu Ile Tyr Ser Thr Ser Asn Leu Ala Ser Gly Val
            500                 505                 510 cca agc aga ttc agc ggt agc ggt agc ggt acc gac ttc acc ttc acc      1584
Pro Ser Arg Phe Ser Gly Ser Gly Ser Gly Thr Asp Phe Thr Phe Thr
            515                 520                 525 atc agc agc ctc cag cca gag gac atc gcc acc tac tac tgc cat cag      1632
Ile Ser Ser Leu Gln Pro Glu Asp Ile Ala Thr Tyr Tyr Cys His Gln
            530                 535                 540 tgg agt agt tat ccc acg ttc ggc caa ggg acc aag gtg gag atc aaa      1680
Trp Ser Ser Tyr Pro Thr Phe Gly Gln Gly Thr Lys Val Glu Ile Lys
            545                 550                 555 gtg gat ccc gcc gag ccc aaa tct cct gac aaa act cac aca tgc cca      1728
Val Asp Pro Ala Glu Pro Lys Ser Pro Asp Lys Thr His Thr Cys Pro
560                 565                 570                 575 ccg tgc cca gca cct cca gtc gcg gga ccg tca gtc ttc ctc ttc ccc      1776
Pro Cys Pro Ala Pro Pro Val Ala Gly Pro Ser Val Phe Leu Phe Pro
            580                 585                 590 cca aaa ccc aag gac acc ctc atg atc gcc cgg acc cct gag gtc aca      1824
Pro Lys Pro Lys Asp Thr Leu Met Ile Ala Arg Thr Pro Glu Val Thr
            595                 600                 605 tgc gtg gtg gtg gac gtg agc cac gaa gac cct gag gtc aag ttc aac      1872
Cys Val Val Val Asp Val Ser His Glu Asp Pro Glu Val Lys Phe Asn
            610                 615                 620 tgg tac gtg gac ggc gtg gag gtg cat aat gcc aag aca aag ccg cgg      1920
Trp Tyr Val Asp Gly Val Glu Val His Asn Ala Lys Thr Lys Pro Arg
625                 630                 635 gag gag cag tac aac agc acg tac cgt gtg gtc agc gtc ctc acc gtc      1968
Glu Glu Gln Tyr Asn Ser Thr Tyr Arg Val Val Ser Val Leu Thr Val
640                 645                 650                 655 ctg cac cag gac tgg ctg aat ggc aag gag tac aag tgc aag gtc tcc      2016
Leu His Gln Asp Trp Leu Asn Gly Lys Glu Tyr Lys Cys Lys Val Ser
            660                 665                 670 aac aaa gcc ctc cca gcc ccc atc gag aaa acc atc tcc aaa gcc aaa      2064
Asn Lys Ala Leu Pro Ala Pro Ile Glu Lys Thr Ile Ser Lys Ala Lys
            675                 680                 685 ggg cag ccc cga gaa cca cag gtg tac acc ctg ccc cca tcc cgg gat      2112
Gly Gln Pro Arg Glu Pro Gln Val Tyr Thr Leu Pro Pro Ser Arg Asp
            690                 695                 700 gag ctg acc aag aac cag gtc agc ctg acc tgc ctg gtc aaa ggc ttc      2160
Glu Leu Thr Lys Asn Gln Val Ser Leu Thr Cys Leu Val Lys Gly Phe
705                 710                 715 tat ccc agc gac atc gcc gtg gag tgg gag agc aat ggg cag ccg gag      2208
Tyr Pro Ser Asp Ile Ala Val Glu Trp Glu Ser Asn Gly Gln Pro Glu
720                 725                 730                 735 aac aac tac aag acc acg cct ccc gtg ctg gac tcc gac ggc tcc ttc      2256
Asn Asn Tyr Lys Thr Thr Pro Pro Val Leu Asp Ser Asp Gly Ser Phe
            740                 745                 750 ttc ctc tac agc aag ctc acc gtg gac aag agc agg tgg cag cag ggg      2304
Phe Leu Tyr Ser Lys Leu Thr Val Asp Lys Ser Arg Trp Gln Gln Gly
            755                 760                 765 aac gtc ttc tca tgc tcc gtg atg cat gag gct ctg cac aac cac tac      2352
Asn Val Phe Ser Cys Ser Val Met His Glu Ala Leu His Asn His Tyr
            770                 775                 780 acg cag aag agc ctc tcc ctg tct ccg ggt aaa aaa gat ccc aaa ttt      2400
Thr Gln Lys Ser Leu Ser Leu Ser Pro Gly Lys Lys Asp Pro Lys Phe
            785                 790                 795 tgg gtg ctg gtg gtg gtt ggt gga gtc ctg gct tgc tat agc ttg cta      2448
Trp Val Leu Val Val Val Gly Gly Val Leu Ala Cys Tyr Ser Leu Leu
800                 805                 810                 815
```

-continued

```
gta aca gtg gcc ttt att att ttc tgg gtg agg agt aag agg agc agg    2496
Val Thr Val Ala Phe Ile Ile Phe Trp Val Arg Ser Lys Arg Ser Arg
            820                 825                 830 ctc ctg cac agt gac tac atg aac atg act ccc cgc ccc ggg ccc        2544
Leu Leu His Ser Asp Tyr Met Asn Met Thr Pro Arg Arg Pro Gly Pro
        835                 840                 845 acc cgc aag cat tac cag gcc tat gcc gcc gca cgc gac ttc gca gcc    2592
Thr Arg Lys His Tyr Gln Ala Tyr Ala Ala Ala Arg Asp Phe Ala Ala
    850                 855                 860 tat cgc tcc ctg aga gtg aag ttc agc agg agc gca gac gcc ccc gcg    2640
Tyr Arg Ser Leu Arg Val Lys Phe Ser Arg Ser Ala Asp Ala Pro Ala
865                 870                 875 tac cag cag ggc cag aac cag ctc tat aac gag ctc aat cta gga cga    2688
Tyr Gln Gln Gly Gln Asn Gln Leu Tyr Asn Glu Leu Asn Leu Gly Arg
880                 885                 890                 895 aga gag gag tac gat gtt ttg gac aag aga cgt ggc cgg gac cct gag    2736
Arg Glu Glu Tyr Asp Val Leu Asp Lys Arg Arg Gly Arg Asp Pro Glu
            900                 905                 910 atg ggg gga aag ccg aga agg aag aac cct cag gaa ggc ctg tac aat    2784
Met Gly Gly Lys Pro Arg Arg Lys Asn Pro Gln Glu Gly Leu Tyr Asn
        915                 920                 925 gaa ctg cag aaa gat aag atg gcg gag gcc tac agt gag att ggg atg    2832
Glu Leu Gln Lys Asp Lys Met Ala Glu Ala Tyr Ser Glu Ile Gly Met
    930                 935                 940 aaa ggc gag cgc cgg agg ggc aag ggg cac gat ggc ctt tac cag ggt    2880
Lys Gly Glu Arg Arg Arg Gly Lys Gly His Asp Gly Leu Tyr Gln Gly
945                 950                 955 ctc agt aca gcc acc aag gac acc tac gac gcc ctt cac atg cag gcc    2928
Leu Ser Thr Ala Thr Lys Asp Thr Tyr Asp Ala Leu His Met Gln Ala
960                 965                 970                 975 ctg ccc cct cgc taa                                                 2943
Leu Pro Pro Arg <210> SEQ ID NO 14
<211> LENGTH: 978
<212> TYPE: PRT
<213> ORGANISM: artificial
<220> FEATURE:
<223> OTHER INFORMATION: Synthetic Construct

<400> SEQUENCE: 14

Thr Ala Met Asp Phe Gln Val Gln Ile Phe Ser Phe Leu Leu Ile Ser
1               5                   10                  15

Ala Ser Val Ile Met Ser Arg Met Ala Gln Val Gln Leu Gln Gln Ser
            20                  25                  30

Gly Ala Glu Leu Ala Arg Pro Gly Ala Ser Val Lys Met Ser Cys Lys
        35                  40                  45

Ala Ser Gly Tyr Thr Phe Thr Thr Tyr Thr Ile His Trp Val Arg Arg
    50                  55                  60

Arg Pro Gly His Asp Leu Glu Trp Ile Gly Tyr Ile Asn Pro Ser Ser
65                  70                  75                  80

Gly Cys Ser Asp Tyr Asn Gln Asn Phe Lys Gly Lys Thr Thr Leu Thr
                85                  90                  95

Ala Asp Lys Ser Ser Asn Thr Ala Tyr Met Gln Leu Asn Ser Leu Thr
            100                 105                 110

Ser Glu Asp Ser Ala Val Tyr Tyr Cys Ala Arg Arg Ala Asp Tyr Gly
        115                 120                 125

Asn Tyr Glu Tyr Thr Trp Phe Ala Tyr Trp Gly Gln Gly Thr Thr Val
```

```
                130                 135                 140
Thr Val Ser Ser Ser Gly Gly Ser Gly Gly Gly Ser Gly Gly
145                 150                 155                 160

Gly Gly Ser Val Ile Glu Leu Thr Gln Ser Pro Lys Phe Met Ser Thr
                165                 170                 175

Ser Val Gly Asp Arg Val Asn Val Thr Tyr Lys Ala Ser Gln Asn Val
                180                 185                 190

Gly Thr Asn Val Ala Trp Phe Gln Gln Lys Pro Gly Gln Ser Pro Lys
                195                 200                 205

Val Leu Ile Tyr Ser Ala Ser Tyr Arg Tyr Ser Gly Val Pro Asp Arg
210                 215                 220

Phe Thr Gly Ser Gly Ser Gly Thr Asp Phe Thr Leu Thr Ile Ser Asn
225                 230                 235                 240

Val Gln Ser Glu Asp Leu Ala Glu Tyr Phe Cys Gln Gln Tyr His Thr
                245                 250                 255

Tyr Pro Leu Thr Phe Gly Gly Gly Thr Lys Leu Glu Ile Lys Arg Ser
                260                 265                 270

Asp Pro Gly Gly Gly Gly Ser Gly Gly Gly Gly Ser Gly Gly Gly Gly
                275                 280                 285

Ser Gly Gly Gly Ser Gly Gly Gly Gly Ser Gly Gly Gly Gly Gly Ser
290                 295                 300

Gly Gly Gly Gly Ser Gly Gly Gly Ser Gly Val His Ser Gln Val
305                 310                 315                 320

Gln Leu Gln Glu Ser Gly Pro Gly Leu Val Arg Pro Ser Gln Thr Leu
                325                 330                 335

Ser Leu Thr Cys Thr Val Ser Gly Phe Thr Ile Ser Ser Gly Tyr Ser
                340                 345                 350

Trp His Trp Val Arg Gln Pro Pro Gly Arg Gly Leu Glu Trp Ile Gly
                355                 360                 365

Tyr Ile Gln Tyr Ser Gly Ile Thr Asn Tyr Asn Pro Ser Leu Lys Ser
                370                 375                 380

Arg Val Thr Met Leu Val Asp Thr Ser Lys Asn Gln Phe Ser Leu Arg
385                 390                 395                 400

Leu Ser Ser Val Thr Ala Ala Asp Thr Ala Val Tyr Tyr Cys Ala Arg
                405                 410                 415

Glu Asp Tyr Asp Tyr His Trp Tyr Phe Asp Val Trp Gly Gln Gly Thr
                420                 425                 430

Thr Val Thr Val Ser Ser Gly Gly Gly Gly Ser Gly Gly Gly Gly Ser
                435                 440                 445

Gly Gly Gly Gly Ser Asp Ile Gln Leu Thr Gln Ser Pro Ser Ser Leu
                450                 455                 460

Ser Ala Ser Val Gly Asp Arg Val Thr Ile Thr Cys Ser Thr Ser Ser
465                 470                 475                 480

Ser Val Ser Tyr Met His Trp Tyr Gln Gln Lys Pro Gly Lys Ala Pro
                485                 490                 495

Lys Leu Leu Ile Tyr Ser Thr Ser Asn Leu Ala Ser Gly Val Pro Ser
                500                 505                 510

Arg Phe Ser Gly Ser Gly Ser Gly Thr Asp Phe Thr Phe Thr Ile Ser
                515                 520                 525

Ser Leu Gln Pro Glu Asp Ile Ala Thr Tyr Tyr Cys His Gln Trp Ser
                530                 535                 540

Ser Tyr Pro Thr Phe Gly Gln Gly Thr Lys Val Glu Ile Lys Val Asp
545                 550                 555                 560
```

```
Pro Ala Glu Pro Lys Ser Pro Asp Lys Thr His Thr Cys Pro Pro Cys
            565                 570                 575
Pro Ala Pro Pro Val Ala Gly Pro Ser Val Phe Leu Phe Pro Pro Lys
            580                 585                 590
Pro Lys Asp Thr Leu Met Ile Ala Arg Thr Pro Glu Val Thr Cys Val
            595                 600                 605
Val Val Asp Val Ser His Glu Asp Pro Glu Val Lys Phe Asn Trp Tyr
            610                 615                 620
Val Asp Gly Val Glu Val His Asn Ala Lys Thr Lys Pro Arg Glu Glu
625                 630                 635                 640
Gln Tyr Asn Ser Thr Tyr Arg Val Val Ser Val Leu Thr Val Leu His
            645                 650                 655
Gln Asp Trp Leu Asn Gly Lys Glu Tyr Lys Cys Lys Val Ser Asn Lys
            660                 665                 670
Ala Leu Pro Ala Pro Ile Glu Lys Thr Ile Ser Lys Ala Lys Gly Gln
            675                 680                 685
Pro Arg Glu Pro Gln Val Tyr Thr Leu Pro Pro Ser Arg Asp Glu Leu
            690                 695                 700
Thr Lys Asn Gln Val Ser Leu Thr Cys Leu Val Lys Gly Phe Tyr Pro
705                 710                 715                 720
Ser Asp Ile Ala Val Glu Trp Glu Ser Asn Gly Gln Pro Glu Asn Asn
            725                 730                 735
Tyr Lys Thr Thr Pro Pro Val Leu Asp Ser Asp Gly Ser Phe Phe Leu
            740                 745                 750
Tyr Ser Lys Leu Thr Val Asp Lys Ser Arg Trp Gln Gln Gly Asn Val
            755                 760                 765
Phe Ser Cys Ser Val Met His Glu Ala Leu His Asn His Tyr Thr Gln
            770                 775                 780
Lys Ser Leu Ser Leu Ser Pro Gly Lys Lys Asp Pro Lys Phe Trp Val
785                 790                 795                 800
Leu Val Val Val Gly Gly Val Leu Ala Cys Tyr Ser Leu Leu Val Thr
            805                 810                 815
Val Ala Phe Ile Ile Phe Trp Val Arg Ser Lys Arg Ser Arg Leu Leu
            820                 825                 830
His Ser Asp Tyr Met Asn Met Thr Pro Arg Arg Pro Gly Pro Thr Arg
            835                 840                 845
Lys His Tyr Gln Ala Tyr Ala Ala Arg Asp Phe Ala Ala Tyr Arg
            850                 855                 860
Ser Leu Arg Val Lys Phe Ser Arg Ser Ala Asp Ala Pro Ala Tyr Gln
865                 870                 875                 880
Gln Gly Gln Asn Gln Leu Tyr Asn Glu Leu Asn Leu Gly Arg Arg Glu
            885                 890                 895
Glu Tyr Asp Val Leu Asp Lys Arg Arg Gly Arg Asp Pro Glu Met Gly
            900                 905                 910
Gly Lys Pro Arg Arg Lys Asn Pro Gln Glu Gly Leu Tyr Asn Glu Leu
            915                 920                 925
Gln Lys Asp Lys Met Ala Glu Ala Tyr Ser Glu Ile Gly Met Lys Gly
            930                 935                 940
Glu Arg Arg Arg Gly Lys Gly His Asp Gly Leu Tyr Gln Gly Leu Ser
945                 950                 955                 960
Thr Ala Thr Lys Asp Thr Tyr Asp Ala Leu His Met Gln Ala Leu Pro
            965                 970                 975
```

Pro Arg

<210> SEQ ID NO 15
<211> LENGTH: 25
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (8)..(20)
<223> OTHER INFORMATION: SVFLFPPKPKDTL

<400> SEQUENCE: 15

Pro Glu Leu Leu Gly Gly Pro Xaa Xaa Xaa Xaa Xaa Xaa Xaa Xaa
1               5                   10                  15

Xaa Xaa Xaa Xaa Met Ile Ser Arg Thr
            20                  25

<210> SEQ ID NO 16
<211> LENGTH: 24
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (7)..(19)
<223> OTHER INFORMATION: SVFLFPPKPKDTL

<400> SEQUENCE: 16

Pro Pro Val Ala Gly Pro Xaa Xaa Xaa Xaa Xaa Xaa Xaa Xaa Xaa
1               5                   10                  15

Xaa Xaa Xaa Met Ile Ala Arg Thr
            20

<210> SEQ ID NO 17
<211> LENGTH: 2901
<212> TYPE: DNA
<213> ORGANISM: artificial
<220> FEATURE:
<223> OTHER INFORMATION: synthetic molecule
<220> FEATURE:
<221> NAME/KEY: CDS
<222> LOCATION: (1)..(2901)

<400> SEQUENCE: 17

```
atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tct aga cag gtg aag ctg cag cag tct ggg act gtg ctg      96
Val Ile Met Ser Arg Gln Val Lys Leu Gln Gln Ser Gly Thr Val Leu
            20                  25                  30 gca agg cct ggg gct tcc gtg aag atg tcc tgc aag gct tct ggc tac     144
Ala Arg Pro Gly Ala Ser Val Lys Met Ser Cys Lys Ala Ser Gly Tyr
        35                  40                  45 agg ttt acc aac tac tgg atg cac tgg gta aaa cag agg cct gga cag     192
Arg Phe Thr Asn Tyr Trp Met His Trp Val Lys Gln Arg Pro Gly Gln
    50                  55                  60 ggt cta gaa tgg att ggt gtt att tat cct gga aat agt gat act agc     240
Gly Leu Glu Trp Ile Gly Val Ile Tyr Pro Gly Asn Ser Asp Thr Ser
65                  70                  75                  80 tac aac cag aag ttc aag ggc aag gcc aaa ctg act gca gtc aca tcc     288
Tyr Asn Gln Lys Phe Lys Gly Lys Ala Lys Leu Thr Ala Val Thr Ser
                85                  90                  95
```

```
gcc agc act gcc tac atg gag ctc agc agc ctg aca aat gag gac tct       336
Ala Ser Thr Ala Tyr Met Glu Leu Ser Ser Leu Thr Asn Glu Asp Ser
            100                 105                 110 gcg gtc tat tac tgt aca aga gag gga gaa ggc tct gac tac tgg ggc       384
Ala Val Tyr Tyr Cys Thr Arg Glu Gly Glu Gly Ser Asp Tyr Trp Gly
        115                 120                 125 caa ggg acc acg gtc acc gtc tcc tca ggt gga ggc ggt tca ggc gga       432
Gln Gly Thr Thr Val Thr Val Ser Ser Gly Gly Gly Gly Ser Gly Gly
    130                 135                 140 ggt ggc tct ggc ggt ggc gga tcg caa att gtt ctc acc cag tct cca       480
Gly Gly Ser Gly Gly Gly Gly Ser Gln Ile Val Leu Thr Gln Ser Pro
145                 150                 155                 160 gca acc atg gct gca tct ccc ggg gag aag atc act atc acc tgc agt       528
Ala Thr Met Ala Ala Ser Pro Gly Glu Lys Ile Thr Ile Thr Cys Ser
                165                 170                 175 gcc agc tca agt ata agt tcc aat tac ttg cat tgg tat cag cag aag       576
Ala Ser Ser Ser Ile Ser Ser Asn Tyr Leu His Trp Tyr Gln Gln Lys
            180                 185                 190 cca gga ttc tcc cct aaa ctc ttg att tat agg act tcc aat ctg gct       624
Pro Gly Phe Ser Pro Lys Leu Leu Ile Tyr Arg Thr Ser Asn Leu Ala
        195                 200                 205 tct gga gtc cca gct cgc ttc agt ggc agt ggg tct ggg acc tct tac       672
Ser Gly Val Pro Ala Arg Phe Ser Gly Ser Gly Ser Gly Thr Ser Tyr
    210                 215                 220 tct ctc aca att ggc acc atg gag gct gaa gat gtt gcc act tac tac       720
Ser Leu Thr Ile Gly Thr Met Glu Ala Glu Asp Val Ala Thr Tyr Tyr
225                 230                 235                 240 tgc cag cag ggt agt agt ata ccg tac acg ttc gga ggg ggg acc aag       768
Cys Gln Gln Gly Ser Ser Ile Pro Tyr Thr Phe Gly Gly Gly Thr Lys
                245                 250                 255 ctg gag ctg gcg gcc gca gga ggc ggg ggt tct ggt gga ggc gga agc       816
Leu Glu Leu Ala Ala Ala Gly Gly Gly Gly Ser Gly Gly Gly Gly Ser
            260                 265                 270 ggt ggc ggg ggt tca gga ggc ggg ggt tcc ggt ggt ggc ggc agt ggt       864
Gly Gly Gly Gly Ser Gly Gly Gly Gly Ser Gly Gly Gly Gly Ser Gly
        275                 280                 285 ggt ggc ggc agt ggt ggt ggc ggc agt ggt ggt ggc ggc agt ggt gtc       912
Gly Gly Gly Ser Gly Gly Gly Gly Ser Gly Gly Gly Gly Ser Gly Val
    290                 295                 300 cac tcc cag gtc caa ctg cag gag tca ggt cca ggt ctt gtg aga cct       960
His Ser Gln Val Gln Leu Gln Glu Ser Gly Pro Gly Leu Val Arg Pro
305                 310                 315                 320 agc cag acc ctg agc ctg acc tgc acc gtg tct ggc ttc acc atc agc      1008
Ser Gln Thr Leu Ser Leu Thr Cys Thr Val Ser Gly Phe Thr Ile Ser
                325                 330                 335 agt ggt tat agc tgg cac tgg gtg aga cag cca cct gga cga ggt ctt      1056
Ser Gly Tyr Ser Trp His Trp Val Arg Gln Pro Pro Gly Arg Gly Leu
            340                 345                 350 gag tgg att gga tac ata cag tac agt ggt atc act aac tac aac ccc      1104
Glu Trp Ile Gly Tyr Ile Gln Tyr Ser Gly Ile Thr Asn Tyr Asn Pro
        355                 360                 365 tct ctc aaa agt aga gtg aca atg ctg gta gac acc agc aag aac cag      1152
Ser Leu Lys Ser Arg Val Thr Met Leu Val Asp Thr Ser Lys Asn Gln
    370                 375                 380 ttc agc ctg aga ctc agc agc gtg aca gcc gcc gac acc gcg gtc tat      1200
Phe Ser Leu Arg Leu Ser Ser Val Thr Ala Ala Asp Thr Ala Val Tyr
385                 390                 395                 400 tat tgt gca aga gaa gac tat gat tac cac tgg tac ttc gat gtc tgg      1248
Tyr Cys Ala Arg Glu Asp Tyr Asp Tyr His Trp Tyr Phe Asp Val Trp
                405                 410                 415
```

```
ggc caa ggg acc acg gtc acc gtc tcc tca gga ggt ggt gga tcg ggc    1296
Gly Gln Gly Thr Thr Val Thr Val Ser Ser Gly Gly Gly Ser Gly
            420             425             430 ggt ggc ggg tcg ggt ggc ggc gga tct gac atc cag ctg acc cag agc    1344
Gly Gly Gly Ser Gly Gly Gly Gly Ser Asp Ile Gln Leu Thr Gln Ser
            435             440             445 cca agc agc ctg agc gcc agc gtg ggt gac aga gtg acc atc acc tgt    1392
Pro Ser Ser Leu Ser Ala Ser Val Gly Asp Arg Val Thr Ile Thr Cys
450             455             460 agt acc agc tcg agt gta agt tac atg cac tgg tac cag cag aag cca    1440
Ser Thr Ser Ser Ser Val Ser Tyr Met His Trp Tyr Gln Gln Lys Pro
465             470             475             480 ggt aag gct cca aag ctg ctg atc tac agc aca tcc aac ctg gct tct    1488
Gly Lys Ala Pro Lys Leu Leu Ile Tyr Ser Thr Ser Asn Leu Ala Ser
                485             490             495 ggt gtg cca agc aga ttc agc ggt agc ggt agc ggt acc gac ttc acc    1536
Gly Val Pro Ser Arg Phe Ser Gly Ser Gly Ser Gly Thr Asp Phe Thr
            500             505             510 ttc acc atc agc agc ctc cag cca gag gac atc gcc acc tac tac tgc    1584
Phe Thr Ile Ser Ser Leu Gln Pro Glu Asp Ile Ala Thr Tyr Tyr Cys
            515             520             525 cat cag tgg agt agt tat ccc acg ttc ggc caa ggg acc aag gtg gag    1632
His Gln Trp Ser Ser Tyr Pro Thr Phe Gly Gln Gly Thr Lys Val Glu
            530             535             540 atc aaa gtg gat ccc gcc gag ccc aaa tct cct gac aaa act cac aca    1680
Ile Lys Val Asp Pro Ala Glu Pro Lys Ser Pro Asp Lys Thr His Thr
545             550             555             560 tgc cca ccg tgc cca gca cct cca gtc gcg gga ccg tca gtc ttc ctc    1728
Cys Pro Pro Cys Pro Ala Pro Pro Val Ala Gly Pro Ser Val Phe Leu
                565             570             575 ttc ccc cca aaa ccc aag gac acc ctc atg atc gcc cgg acc cct gag    1776
Phe Pro Pro Lys Pro Lys Asp Thr Leu Met Ile Ala Arg Thr Pro Glu
            580             585             590 gtc aca tgc gtg gtg gtg gac gtg agc cac gaa gac cct gag gtc aag    1824
Val Thr Cys Val Val Val Asp Val Ser His Glu Asp Pro Glu Val Lys
            595             600             605 ttc aac tgg tac gtg gac ggc gtg gag gtg cat aat gcc aag aca aag    1872
Phe Asn Trp Tyr Val Asp Gly Val Glu Val His Asn Ala Lys Thr Lys
            610             615             620 ccg cgg gag gag cag tac aac agc acg tac cgt gtg gtc agc gtc ctc    1920
Pro Arg Glu Glu Gln Tyr Asn Ser Thr Tyr Arg Val Val Ser Val Leu
625             630             635             640 acc gtc ctg cac cag gac tgg ctg aat ggc aag gag tac aag tgc aag    1968
Thr Val Leu His Gln Asp Trp Leu Asn Gly Lys Glu Tyr Lys Cys Lys
                645             650             655 gtc tcc aac aaa gcc ctc cca gcc ccc atc gag aaa acc atc tcc aaa    2016
Val Ser Asn Lys Ala Leu Pro Ala Pro Ile Glu Lys Thr Ile Ser Lys
            660             665             670 gcc aaa ggg cag ccc cga gaa cca cag gtg tac acc ctg ccc cca tcc    2064
Ala Lys Gly Gln Pro Arg Glu Pro Gln Val Tyr Thr Leu Pro Pro Ser
            675             680             685 cgg gat gag ctg acc aag aac cag gtc agc ctg acc tgc ctg gtc aaa    2112
Arg Asp Glu Leu Thr Lys Asn Gln Val Ser Leu Thr Cys Leu Val Lys
690             695             700 ggc ttc tat ccc agc gac atc gcc gtg gag tgg gag agc aat ggg cag    2160
Gly Phe Tyr Pro Ser Asp Ile Ala Val Glu Trp Glu Ser Asn Gly Gln
705             710             715             720 ccg gag aac aac tac aag acc acg cct ccc gtg ctg gac tcc gac ggc    2208
Pro Glu Asn Asn Tyr Lys Thr Thr Pro Pro Val Leu Asp Ser Asp Gly
```

```
                          725                 730                 735
tcc ttc ttc ctc tac agc aag ctc acc gtg gac aag agc agg tgg cag    2256
Ser Phe Phe Leu Tyr Ser Lys Leu Thr Val Asp Lys Ser Arg Trp Gln
            740                 745                 750 cag ggg aac gtc ttc tca tgc tcc gtg atg cat gag gct ctg cac aac    2304
Gln Gly Asn Val Phe Ser Cys Ser Val Met His Glu Ala Leu His Asn
        755                 760                 765 cac tac acg cag aag agc ctc tcc ctg tct ccg ggt aaa aaa gat ccc    2352
His Tyr Thr Gln Lys Ser Leu Ser Leu Ser Pro Gly Lys Lys Asp Pro
    770                 775                 780 aaa ttt tgg gtg ctg gtg gtg gtt ggt gga gtc ctg gct tgc tat agc    2400
Lys Phe Trp Val Leu Val Val Val Gly Gly Val Leu Ala Cys Tyr Ser
785                 790                 795                 800 ttg cta gta aca gtg gcc ttt att att ttc tgg gtg agg agt aag agg    2448
Leu Leu Val Thr Val Ala Phe Ile Ile Phe Trp Val Arg Ser Lys Arg
                805                 810                 815 agc agg ctc ctg cac agt gac tac atg aac atg act ccc cgc cgc ccc    2496
Ser Arg Leu Leu His Ser Asp Tyr Met Asn Met Thr Pro Arg Arg Pro
            820                 825                 830 ggg ccc acc cgc aag cat tac cag gcc tat gcc gcc gca cgc gac ttc    2544
Gly Pro Thr Arg Lys His Tyr Gln Ala Tyr Ala Ala Ala Arg Asp Phe
        835                 840                 845 gca gcc tat cgc tcc ctg aga gtg aag ttc agc agg agc gca gac gcc    2592
Ala Ala Tyr Arg Ser Leu Arg Val Lys Phe Ser Arg Ser Ala Asp Ala
    850                 855                 860 ccc gcg tac cag cag ggc cag aac cag ctc tat aac gag ctc aat cta    2640
Pro Ala Tyr Gln Gln Gly Gln Asn Gln Leu Tyr Asn Glu Leu Asn Leu
865                 870                 875                 880 gga cga aga gag gag tac gat gtt ttg gac aag aga cgt ggc cgg gac    2688
Gly Arg Arg Glu Glu Tyr Asp Val Leu Asp Lys Arg Arg Gly Arg Asp
                885                 890                 895 cct gag atg ggg gga aag ccg aga agg aag aac cct cag gaa ggc ctg    2736
Pro Glu Met Gly Gly Lys Pro Arg Arg Lys Asn Pro Gln Glu Gly Leu
            900                 905                 910 tac aat gaa ctg cag aaa gat aag atg gcg gag gcc tac agt gag att    2784
Tyr Asn Glu Leu Gln Lys Asp Lys Met Ala Glu Ala Tyr Ser Glu Ile
        915                 920                 925 ggg atg aaa ggc gag cgc cgg agg ggc aag ggg cac gat ggc ctt tac    2832
Gly Met Lys Gly Glu Arg Arg Arg Gly Lys Gly His Asp Gly Leu Tyr
    930                 935                 940 cag ggt ctc agt aca gcc acc aag gac acc tac gac gcc ctt cac atg    2880
Gln Gly Leu Ser Thr Ala Thr Lys Asp Thr Tyr Asp Ala Leu His Met
945                 950                 955                 960 cag gcc ctg ccc cct cgc taa                                        2901
Gln Ala Leu Pro Pro Arg
                965

<210> SEQ ID NO 18
<211> LENGTH: 966
<212> TYPE: PRT
<213> ORGANISM: artificial
<220> FEATURE:
<223> OTHER INFORMATION: Synthetic Construct

<400> SEQUENCE: 18

Met Asp Phe Gln Val Gln Ile Phe Ser Phe Leu Leu Ile Ser Ala Ser
1               5                   10                  15

Val Ile Met Ser Arg Gln Val Lys Leu Gln Gln Ser Gly Thr Val Leu
            20                  25                  30

Ala Arg Pro Gly Ala Ser Val Lys Met Ser Cys Lys Ala Ser Gly Tyr
```

```
            35                  40                  45
Arg Phe Thr Asn Tyr Trp Met His Trp Val Lys Gln Arg Pro Gly Gln
 50                  55                  60

Gly Leu Glu Trp Ile Gly Val Ile Tyr Pro Gly Asn Ser Asp Thr Ser
 65                  70                  75                  80

Tyr Asn Gln Lys Phe Lys Gly Lys Ala Lys Leu Thr Ala Val Thr Ser
                 85                  90                  95

Ala Ser Thr Ala Tyr Met Glu Leu Ser Ser Leu Thr Asn Glu Asp Ser
                100                 105                 110

Ala Val Tyr Tyr Cys Thr Arg Glu Gly Glu Ser Asp Tyr Trp Gly
                115                 120                 125

Gln Gly Thr Thr Val Thr Val Ser Ser Gly Gly Gly Ser Gly Gly
                130                 135                 140

Gly Gly Ser Gly Gly Gly Ser Gln Ile Val Leu Thr Gln Ser Pro
145                 150                 155                 160

Ala Thr Met Ala Ala Ser Pro Gly Glu Lys Ile Thr Ile Thr Cys Ser
                165                 170                 175

Ala Ser Ser Ser Ile Ser Ser Asn Tyr Leu His Trp Tyr Gln Gln Lys
                180                 185                 190

Pro Gly Phe Ser Pro Lys Leu Leu Ile Tyr Arg Thr Ser Asn Leu Ala
                195                 200                 205

Ser Gly Val Pro Ala Arg Phe Ser Gly Ser Gly Ser Gly Thr Ser Tyr
210                 215                 220

Ser Leu Thr Ile Gly Thr Met Glu Ala Glu Asp Val Ala Thr Tyr Tyr
225                 230                 235                 240

Cys Gln Gln Gly Ser Ser Ile Pro Tyr Thr Phe Gly Gly Gly Thr Lys
                245                 250                 255

Leu Glu Leu Ala Ala Ala Gly Gly Gly Ser Gly Gly Gly Gly Ser
                260                 265                 270

Gly Gly Gly Gly Ser Gly Gly Gly Ser Gly Gly Gly Gly Ser Gly
                275                 280                 285

Gly Gly Gly Ser Gly Gly Gly Gly Ser Gly Gly Gly Ser Gly Val
                290                 295                 300

His Ser Gln Val Gln Leu Gln Glu Ser Gly Pro Gly Leu Val Arg Pro
305                 310                 315                 320

Ser Gln Thr Leu Ser Leu Thr Cys Thr Val Ser Gly Phe Thr Ile Ser
                325                 330                 335

Ser Gly Tyr Ser Trp His Trp Val Arg Gln Pro Pro Gly Arg Gly Leu
                340                 345                 350

Glu Trp Ile Gly Tyr Ile Gln Tyr Ser Gly Ile Thr Asn Tyr Asn Pro
                355                 360                 365

Ser Leu Lys Ser Arg Val Thr Met Leu Val Asp Thr Ser Lys Asn Gln
                370                 375                 380

Phe Ser Leu Arg Leu Ser Ser Val Thr Ala Ala Asp Thr Ala Val Tyr
385                 390                 395                 400

Tyr Cys Ala Arg Glu Asp Tyr Asp Tyr His Trp Tyr Phe Asp Val Trp
                405                 410                 415

Gly Gln Gly Thr Thr Val Thr Val Ser Ser Gly Gly Gly Gly Ser Gly
                420                 425                 430

Gly Gly Ser Gly Gly Gly Gly Ser Asp Ile Gln Leu Thr Gln Ser
                435                 440                 445

Pro Ser Ser Leu Ser Ala Ser Val Gly Asp Arg Val Thr Ile Thr Cys
450                 455                 460
```

```
Ser Thr Ser Ser Ser Val Ser Tyr Met His Trp Tyr Gln Gln Lys Pro
465                 470                 475                 480

Gly Lys Ala Pro Lys Leu Leu Ile Tyr Ser Thr Ser Asn Leu Ala Ser
            485                 490                 495

Gly Val Pro Ser Arg Phe Ser Gly Ser Gly Ser Gly Thr Asp Phe Thr
        500                 505                 510

Phe Thr Ile Ser Ser Leu Gln Pro Glu Asp Ile Ala Thr Tyr Tyr Cys
        515                 520                 525

His Gln Trp Ser Ser Tyr Pro Thr Phe Gly Gln Gly Thr Lys Val Glu
    530                 535                 540

Ile Lys Val Asp Pro Ala Glu Pro Lys Ser Pro Asp Lys Thr His Thr
545                 550                 555                 560

Cys Pro Pro Cys Pro Ala Pro Pro Val Ala Gly Pro Ser Val Phe Leu
                565                 570                 575

Phe Pro Pro Lys Pro Lys Asp Thr Leu Met Ile Ala Arg Thr Pro Glu
            580                 585                 590

Val Thr Cys Val Val Val Asp Val Ser His Glu Asp Pro Glu Val Lys
        595                 600                 605

Phe Asn Trp Tyr Val Asp Gly Val Glu Val His Asn Ala Lys Thr Lys
    610                 615                 620

Pro Arg Glu Glu Gln Tyr Asn Ser Thr Tyr Arg Val Val Ser Val Leu
625                 630                 635                 640

Thr Val Leu His Gln Asp Trp Leu Asn Gly Lys Glu Tyr Lys Cys Lys
                645                 650                 655

Val Ser Asn Lys Ala Leu Pro Ala Pro Ile Glu Lys Thr Ile Ser Lys
            660                 665                 670

Ala Lys Gly Gln Pro Arg Glu Pro Gln Val Tyr Thr Leu Pro Pro Ser
        675                 680                 685

Arg Asp Glu Leu Thr Lys Asn Gln Val Ser Leu Thr Cys Leu Val Lys
    690                 695                 700

Gly Phe Tyr Pro Ser Asp Ile Ala Val Glu Trp Glu Ser Asn Gly Gln
705                 710                 715                 720

Pro Glu Asn Asn Tyr Lys Thr Thr Pro Pro Val Leu Asp Ser Asp Gly
                725                 730                 735

Ser Phe Phe Leu Tyr Ser Lys Leu Thr Val Asp Lys Ser Arg Trp Gln
            740                 745                 750

Gln Gly Asn Val Phe Ser Cys Ser Val Met His Glu Ala Leu His Asn
        755                 760                 765

His Tyr Thr Gln Lys Ser Leu Ser Leu Ser Pro Gly Lys Lys Asp Pro
    770                 775                 780

Lys Phe Trp Val Leu Val Val Val Gly Gly Val Leu Ala Cys Tyr Ser
785                 790                 795                 800

Leu Leu Val Thr Val Ala Phe Ile Ile Phe Trp Val Arg Ser Lys Arg
                805                 810                 815

Ser Arg Leu Leu His Ser Asp Tyr Met Asn Met Thr Pro Arg Arg Pro
            820                 825                 830

Gly Pro Thr Arg Lys His Tyr Gln Ala Tyr Ala Ala Ala Arg Asp Phe
        835                 840                 845

Ala Ala Tyr Arg Ser Leu Arg Val Lys Phe Ser Arg Ser Ala Asp Ala
    850                 855                 860

Pro Ala Tyr Gln Gln Gly Gln Asn Gln Leu Tyr Asn Glu Leu Asn Leu
865                 870                 875                 880
```

-continued

```
Gly Arg Arg Glu Glu Tyr Asp Val Leu Asp Lys Arg Gly Arg Asp
                    885                 890                 895

Pro Glu Met Gly Gly Lys Pro Arg Arg Lys Asn Pro Gln Glu Gly Leu
            900                 905                 910

Tyr Asn Glu Leu Gln Lys Asp Lys Met Ala Glu Ala Tyr Ser Glu Ile
        915                 920                 925

Gly Met Lys Gly Glu Arg Arg Arg Gly Lys Gly His Asp Gly Leu Tyr
    930                 935                 940

Gln Gly Leu Ser Thr Ala Thr Lys Asp Thr Tyr Asp Ala Leu His Met
945                 950                 955                 960

Gln Ala Leu Pro Pro Arg
                965
```

<210> SEQ ID NO 19
<211> LENGTH: 2937
<212> TYPE: DNA
<213> ORGANISM: artificial
<220> FEATURE:
<223> OTHER INFORMATION: synthetic molecule
<220> FEATURE:
<221> NAME/KEY: CDS
<222> LOCATION: (1)..(2937)

<400> SEQUENCE: 19

```
atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tct aga atg gcc cag gtg caa ctg cag cag tca ggg gct      96
Val Ile Met Ser Arg Met Ala Gln Val Gln Leu Gln Gln Ser Gly Ala
            20                  25                  30 gag ctg gct aga cct ggg gct tca gtg aag atg tcc tgc aag gct tct     144
Glu Leu Ala Arg Pro Gly Ala Ser Val Lys Met Ser Cys Lys Ala Ser
        35                  40                  45 ggc tac acc ttt act acc tac aca ata cac tgg gta aga cgg agg cct     192
Gly Tyr Thr Phe Thr Thr Tyr Thr Ile His Trp Val Arg Arg Arg Pro
    50                  55                  60 gga cac gat ctg gaa tgg att gga tac att aat cct agc agt gga tgt     240
Gly His Asp Leu Glu Trp Ile Gly Tyr Ile Asn Pro Ser Ser Gly Cys
65                  70                  75                  80 tct gac tac aat caa aac ttc aag ggc aag acc aca ttg act gca gac     288
Ser Asp Tyr Asn Gln Asn Phe Lys Gly Lys Thr Thr Leu Thr Ala Asp
                85                  90                  95 aag tcc tcc aac aca gcc tac atg caa ctg aac agc ctg aca tct gag     336
Lys Ser Ser Asn Thr Ala Tyr Met Gln Leu Asn Ser Leu Thr Ser Glu
            100                 105                 110 gac tct gcg gtc tat tac tgt gca aga aga gcg gac tat ggt aac tac     384
Asp Ser Ala Val Tyr Tyr Cys Ala Arg Arg Ala Asp Tyr Gly Asn Tyr
        115                 120                 125 gaa tat acc tgg ttt gct tac tgg ggc caa ggg acc acg gtc acc gtc     432
Glu Tyr Thr Trp Phe Ala Tyr Trp Gly Gln Gly Thr Thr Val Thr Val
    130                 135                 140 tcc tca agt gga ggc ggt tca ggt gga ggt ggc tct ggc ggt ggc gga     480
Ser Ser Ser Gly Gly Gly Ser Gly Gly Gly Gly Ser Gly Gly Gly Gly
145                 150                 155                 160 tcg gtc atc gag ctc act cag tct cca aaa ttc atg tcc aca tca gta     528
Ser Val Ile Glu Leu Thr Gln Ser Pro Lys Phe Met Ser Thr Ser Val
                165                 170                 175 gga gac agg gtc aac gtc acc tac aag gcc agt cag aat gtg ggt act     576
Gly Asp Arg Val Asn Val Thr Tyr Lys Ala Ser Gln Asn Val Gly Thr
            180                 185                 190
```

-continued

| | |
|---|---|
| aat gta gcc tgg ttt caa caa aaa cca ggg caa tct cct aaa gtt ctg<br>Asn Val Ala Trp Phe Gln Gln Lys Pro Gly Gln Ser Pro Lys Val Leu<br>        195                      200                        205 | 624 |
| att tac tcg gca tct tac cga tac agt gga gtc cct gat cgc ttc aca<br>Ile Tyr Ser Ala Ser Tyr Arg Tyr Ser Gly Val Pro Asp Arg Phe Thr<br>   210                      215                      220 | 672 |
| ggc agt gga tct gga aca gat ttc act ctc acc atc agc aat gtg cag<br>Gly Ser Gly Ser Gly Thr Asp Phe Thr Leu Thr Ile Ser Asn Val Gln<br>225                      230                      235                      240 | 720 |
| tct gaa gac ttg gca gag tat ttc tgt cag caa tat cac acc tat cct<br>Ser Glu Asp Leu Ala Glu Tyr Phe Cys Gln Gln Tyr His Thr Tyr Pro<br>                245                      250                      255 | 768 |
| ctc acg ttc gga ggg ggc acc aag ctg gaa atc aaa cgg gcg gcc gct<br>Leu Thr Phe Gly Gly Gly Thr Lys Leu Glu Ile Lys Arg Ala Ala Ala<br>            260                      265                      270 | 816 |
| ggt ggc ggg gga tct gga gga ggt ggt tcc gga gga ggt ggt tca gga<br>Gly Gly Gly Gly Ser Gly Gly Gly Gly Ser Gly Gly Gly Gly Ser Gly<br>                275                      280                      285 | 864 |
| ggt ggc ggc tcc gga gga ggt gga tca gga ggc ggt ggc agc ggc ggc<br>Gly Gly Gly Ser Gly Gly Gly Gly Ser Gly Gly Gly Gly Ser Gly Gly<br>            290                      295                      300 | 912 |
| gga gga tct ggt ggc ggt ggc tcc gtc gac atg gcg cag gtc cag ctc<br>Gly Gly Ser Gly Gly Gly Gly Ser Val Asp Met Ala Gln Val Gln Leu<br>305                      310                      315                      320 | 960 |
| cag gag tcc ggc gga ggc ctg gtg cag cca ggc ggg tcc ctg aag ctg<br>Gln Glu Ser Gly Gly Gly Leu Val Gln Pro Gly Gly Ser Leu Lys Leu<br>                  325                      330                      335 | 1008 |
| agc tgt gct gca tcc ggt ttt acc ttt tcc agt tac gga atg tcc tgg<br>Ser Cys Ala Ala Ser Gly Phe Thr Phe Ser Ser Tyr Gly Met Ser Trp<br>                340                      345                      350 | 1056 |
| gtt cgc cag acc ccc gat aag cgg ctg gaa ctg gtg gcg aca atc aac<br>Val Arg Gln Thr Pro Asp Lys Arg Leu Glu Leu Val Ala Thr Ile Asn<br>                355                      360                      365 | 1104 |
| tcc aat ggc gga tct act tat tac cca gat tct gtt aaa ggc cgt ttt<br>Ser Asn Gly Gly Ser Thr Tyr Tyr Pro Asp Ser Val Lys Gly Arg Phe<br>   370                      375                      380 | 1152 |
| acc atc tcc agg gat aac gcc aaa aac acc ctg tat ctg cag atg tct<br>Thr Ile Ser Arg Asp Asn Ala Lys Asn Thr Leu Tyr Leu Gln Met Ser<br>385                      390                      395                      400 | 1200 |
| tct ttg aag agt gag gac act gct atg tac tat tgc gcc cgg gat cgt<br>Ser Leu Lys Ser Glu Asp Thr Ala Met Tyr Tyr Cys Ala Arg Asp Arg<br>                  405                      410                      415 | 1248 |
| gac ggc tac gat gaa ggt ttc gac tac tgg gga cag ggc aca acc gtc<br>Asp Gly Tyr Asp Glu Gly Phe Asp Tyr Trp Gly Gln Gly Thr Thr Val<br>                420                      425                      430 | 1296 |
| act gtc tct tcc ggc ggt ggt ggc agc ggc ggc ggg gga agc ggc ggg<br>Thr Val Ser Ser Gly Gly Gly Gly Ser Gly Gly Gly Gly Ser Gly Gly<br>                  435                      440                      445 | 1344 |
| ggt ggt tcc gac atc gag ctc acc caa tcc ccc tcc atc atg tcc gcc<br>Gly Gly Ser Asp Ile Glu Leu Thr Gln Ser Pro Ser Ile Met Ser Ala<br>            450                      455                      460 | 1392 |
| tcc cca ggc gag aag gtc acc atg acc tgc tct gct tct tcc gtg<br>Ser Pro Gly Glu Lys Val Thr Met Thr Cys Ser Ala Ser Ser Val<br>465                      470                      475                      480 | 1440 |
| tct tac atg cat tgg tac cag cag aaa tct ggt acc tct ccg aaa cgc<br>Ser Tyr Met His Trp Tyr Gln Gln Lys Ser Gly Thr Ser Pro Lys Arg<br>                  485                      490                      495 | 1488 |
| tgg atc tat gac acc tct aag ttg gct tcc ggg gtg cca gcc cgg ttc<br>Trp Ile Tyr Asp Thr Ser Lys Leu Ala Ser Gly Val Pro Ala Arg Phe<br>                500                      505                      510 | 1536 |

```
tct ggc agc gga agt gga acc tcc tac tcc ctc act att tct tct atg      1584
Ser Gly Ser Gly Ser Gly Thr Ser Tyr Ser Leu Thr Ile Ser Ser Met
        515                 520                 525 gag gct gaa gac gcc gcg acc tat tat tgt cag caa tgg agc agc aac      1632
Glu Ala Glu Asp Ala Ala Thr Tyr Tyr Cys Gln Gln Trp Ser Ser Asn
530                 535                 540 ccc cct act ctg ggg cgc cgt act cag ctg cag ctg aaa cgc gcg gat      1680
Pro Pro Thr Leu Gly Arg Arg Thr Gln Leu Gln Leu Lys Arg Ala Asp
545                 550                 555                 560 ccc gcc gag ccc aaa tct cct gac aaa act cac aca tgc cca ccg tgc      1728
Pro Ala Glu Pro Lys Ser Pro Asp Lys Thr His Thr Cys Pro Pro Cys
                565                 570                 575 cca gca cct cca gtc gcg gga ccg tca gtc ttc ctc ttc ccc cca aaa      1776
Pro Ala Pro Pro Val Ala Gly Pro Ser Val Phe Leu Phe Pro Pro Lys
            580                 585                 590 ccc aag gac acc ctc atg atc gcc cgg acc cct gag gtc aca tgc gtg      1824
Pro Lys Asp Thr Leu Met Ile Ala Arg Thr Pro Glu Val Thr Cys Val
        595                 600                 605 gtg gtg gac gtg agc cac gaa gac cct gag gtc aag ttc aac tgg tac      1872
Val Val Asp Val Ser His Glu Asp Pro Glu Val Lys Phe Asn Trp Tyr
    610                 615                 620 gtg gac ggc gtg gag gtg cat aat gcc aag aca aag ccg cgg gag gag      1920
Val Asp Gly Val Glu Val His Asn Ala Lys Thr Lys Pro Arg Glu Glu
625                 630                 635                 640 cag tac aac agc acg tac cgt gtg gtc agc gtc ctc acc gtc ctg cac      1968
Gln Tyr Asn Ser Thr Tyr Arg Val Val Ser Val Leu Thr Val Leu His
                645                 650                 655 cag gac tgg ctg aat ggc aag gag tac aag tgc aag gtc tcc aac aaa      2016
Gln Asp Trp Leu Asn Gly Lys Glu Tyr Lys Cys Lys Val Ser Asn Lys
            660                 665                 670 gcc ctc cca gcc ccc atc gag aaa acc atc tcc aaa gcc aaa ggg cag      2064
Ala Leu Pro Ala Pro Ile Glu Lys Thr Ile Ser Lys Ala Lys Gly Gln
        675                 680                 685 ccc cga gaa cca cag gtg tac acc ctg ccc cca tcc cgg gat gag ctg      2112
Pro Arg Glu Pro Gln Val Tyr Thr Leu Pro Pro Ser Arg Asp Glu Leu
    690                 695                 700 acc aag aac cag gtc agc ctg acc tgc ctg gtc aaa ggc ttc tat ccc      2160
Thr Lys Asn Gln Val Ser Leu Thr Cys Leu Val Lys Gly Phe Tyr Pro
705                 710                 715                 720 agc gac atc gcc gtg gag tgg gag agc aat ggg cag ccg gag aac aac      2208
Ser Asp Ile Ala Val Glu Trp Glu Ser Asn Gly Gln Pro Glu Asn Asn
                725                 730                 735 tac aag acc acg cct ccc gtg ctg gac tcc gac ggc tcc ttc ttc ctc      2256
Tyr Lys Thr Thr Pro Pro Val Leu Asp Ser Asp Gly Ser Phe Phe Leu
            740                 745                 750 tac agc aag ctc acc gtg gac aag agc agg tgg cag cag ggg aac gtc      2304
Tyr Ser Lys Leu Thr Val Asp Lys Ser Arg Trp Gln Gln Gly Asn Val
        755                 760                 765 ttc tca tgc tcc gtg atg cat gag gct ctg cac aac cac tac acg cag      2352
Phe Ser Cys Ser Val Met His Glu Ala Leu His Asn His Tyr Thr Gln
    770                 775                 780 aag agc ctc tcc ctg tct ccg ggt aaa aaa gat ccc aaa ttt tgg gtg      2400
Lys Ser Leu Ser Leu Ser Pro Gly Lys Lys Asp Pro Lys Phe Trp Val
785                 790                 795                 800 ctg gtg gtg gtt ggt gga gtc ctg gct tgc tat agc ttg cta gta aca      2448
Leu Val Val Val Gly Gly Val Leu Ala Cys Tyr Ser Leu Leu Val Thr
                805                 810                 815 gtg gcc ttt att att ttc tgg gtg agg agt aag agg agc agg ctc ctg      2496
Val Ala Phe Ile Ile Phe Trp Val Arg Ser Lys Arg Ser Arg Leu Leu
```

```
                    820                 825                 830
cac agt gac tac atg aac atg act ccc cgc cgc ccc ggg ccc acc cgc      2544
His Ser Asp Tyr Met Asn Met Thr Pro Arg Arg Pro Gly Pro Thr Arg
            835                 840                 845 aag cat tac cag gcc tat gcc gcc gca cgc gac ttc gca gcc tat cgc      2592
Lys His Tyr Gln Ala Tyr Ala Ala Ala Arg Asp Phe Ala Ala Tyr Arg
    850                 855                 860 tcc ctg aga gtg aag ttc agc agg agc gca gac gcc ccc gcg tac cag      2640
Ser Leu Arg Val Lys Phe Ser Arg Ser Ala Asp Ala Pro Ala Tyr Gln
865                 870                 875                 880 cag ggc cag aac cag ctc tat aac gag ctc aat cta gga cga aga gag      2688
Gln Gly Gln Asn Gln Leu Tyr Asn Glu Leu Asn Leu Gly Arg Arg Glu
                885                 890                 895 gag tac gat gtt ttg gac aag aga cgt ggc cgg gac cct gag atg ggg      2736
Glu Tyr Asp Val Leu Asp Lys Arg Arg Gly Arg Asp Pro Glu Met Gly
            900                 905                 910 gga aag ccg aga agg aag aac cct cag gaa ggc ctg tac aat gaa ctg      2784
Gly Lys Pro Arg Arg Lys Asn Pro Gln Glu Gly Leu Tyr Asn Glu Leu
    915                 920                 925 cag aaa gat aag atg gcg gag gcc tac agt gag att ggg atg aaa ggc      2832
Gln Lys Asp Lys Met Ala Glu Ala Tyr Ser Glu Ile Gly Met Lys Gly
930                 935                 940 gag cgc cgg agg ggc aag ggg cac gat ggc ctt tac cag ggt ctc agt      2880
Glu Arg Arg Arg Gly Lys Gly His Asp Gly Leu Tyr Gln Gly Leu Ser
945                 950                 955                 960 aca gcc acc aag gac acc tac gac gcc ctt cac atg cag gcc ctg ccc      2928
Thr Ala Thr Lys Asp Thr Tyr Asp Ala Leu His Met Gln Ala Leu Pro
                965                 970                 975 cct cgc taa                                                          2937
Pro Arg <210> SEQ ID NO 20
<211> LENGTH: 978
<212> TYPE: PRT
<213> ORGANISM: artificial
<220> FEATURE:
<223> OTHER INFORMATION: Synthetic Construct

<400> SEQUENCE: 20

Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Thr Tyr Thr Ile His Trp Val Arg Arg Pro
    50                  55                  60

Gly His Asp Leu Glu Trp Ile Gly Tyr Ile Asn Pro Ser Ser Gly Cys
65                  70                  75                  80

Ser Asp Tyr Asn Gln Asn Phe Lys Gly Lys Thr Thr Leu Thr Ala Asp
                85                  90                  95

Lys Ser Ser Asn Thr Ala Tyr Met Gln Leu Asn Ser Leu Thr Ser Glu
            100                 105                 110

Asp Ser Ala Val Tyr Tyr Cys Ala Arg Arg Ala Asp Tyr Gly Asn Tyr
        115                 120                 125

Glu Tyr Thr Trp Phe Ala Tyr Trp Gly Gln Gly Thr Thr Val Thr Val
    130                 135                 140

Ser Ser Ser Gly Gly Gly Ser Gly Gly Gly Gly Ser Gly Gly Gly Gly
145                 150                 155                 160
```

```
Ser Val Ile Glu Leu Thr Gln Ser Pro Lys Phe Met Ser Thr Ser Val
                165                 170                 175

Gly Asp Arg Val Asn Val Thr Tyr Lys Ala Ser Gln Asn Val Gly Thr
            180                 185                 190

Asn Val Ala Trp Phe Gln Gln Lys Pro Gly Gln Ser Pro Lys Val Leu
        195                 200                 205

Ile Tyr Ser Ala Ser Tyr Arg Tyr Ser Gly Val Pro Asp Arg Phe Thr
    210                 215                 220

Gly Ser Gly Ser Gly Thr Asp Phe Thr Leu Thr Ile Ser Asn Val Gln
225                 230                 235                 240

Ser Glu Asp Leu Ala Glu Tyr Phe Cys Gln Gln Tyr His Thr Tyr Pro
            245                 250                 255

Leu Thr Phe Gly Gly Gly Thr Lys Leu Glu Ile Lys Arg Ala Ala Ala
        260                 265                 270

Gly Gly Gly Gly Ser Gly Gly Gly Gly Ser Gly Gly Gly Gly Ser Gly
    275                 280                 285

Gly Gly Gly Ser Gly Gly Gly Gly Ser Gly Gly Gly Gly Ser Gly Gly
        290                 295                 300

Gly Gly Ser Gly Gly Gly Gly Ser Val Asp Met Ala Gln Val Gln Leu
305                 310                 315                 320

Gln Glu Ser Gly Gly Gly Leu Val Gln Pro Gly Gly Ser Leu Lys Leu
            325                 330                 335

Ser Cys Ala Ala Ser Gly Phe Thr Phe Ser Ser Tyr Gly Met Ser Trp
        340                 345                 350

Val Arg Gln Thr Pro Asp Lys Arg Leu Glu Leu Val Ala Thr Ile Asn
    355                 360                 365

Ser Asn Gly Gly Ser Thr Tyr Tyr Pro Asp Ser Val Lys Gly Arg Phe
370                 375                 380

Thr Ile Ser Arg Asp Asn Ala Lys Asn Thr Leu Tyr Leu Gln Met Ser
385                 390                 395                 400

Ser Leu Lys Ser Glu Asp Thr Ala Met Tyr Tyr Cys Ala Arg Asp Arg
            405                 410                 415

Asp Gly Tyr Asp Glu Gly Phe Asp Tyr Trp Gly Gln Gly Thr Thr Val
        420                 425                 430

Thr Val Ser Ser Gly Gly Gly Gly Ser Gly Gly Gly Gly Ser Gly Gly
    435                 440                 445

Gly Gly Ser Asp Ile Glu Leu Thr Gln Ser Pro Ser Ile Met Ser Ala
    450                 455                 460

Ser Pro Gly Glu Lys Val Thr Met Thr Cys Ser Ala Ser Ser Ser Val
465                 470                 475                 480

Ser Tyr Met His Trp Tyr Gln Gln Lys Ser Gly Thr Ser Pro Lys Arg
            485                 490                 495

Trp Ile Tyr Asp Thr Ser Lys Leu Ala Ser Gly Val Pro Ala Arg Phe
        500                 505                 510

Ser Gly Ser Gly Ser Gly Thr Ser Tyr Ser Leu Thr Ile Ser Ser Met
    515                 520                 525

Glu Ala Glu Asp Ala Ala Thr Tyr Tyr Cys Gln Gln Trp Ser Ser Asn
530                 535                 540

Pro Pro Thr Leu Gly Arg Arg Thr Gln Leu Gln Leu Lys Arg Ala Asp
545                 550                 555                 560

Pro Ala Glu Pro Lys Ser Pro Asp Lys Thr His Thr Cys Pro Pro Cys
            565                 570                 575
```

Pro Ala Pro Pro Val Ala Gly Pro Ser Val Phe Leu Phe Pro Pro Lys
            580                 585                 590

Pro Lys Asp Thr Leu Met Ile Ala Arg Thr Pro Glu Val Thr Cys Val
        595                 600                 605

Val Val Asp Val Ser His Glu Asp Pro Glu Val Lys Phe Asn Trp Tyr
    610                 615                 620

Val Asp Gly Val Glu Val His Asn Ala Lys Thr Lys Pro Arg Glu Glu
625                 630                 635                 640

Gln Tyr Asn Ser Thr Tyr Arg Val Val Ser Val Leu Thr Val Leu His
                645                 650                 655

Gln Asp Trp Leu Asn Gly Lys Glu Tyr Lys Cys Lys Val Ser Asn Lys
            660                 665                 670

Ala Leu Pro Ala Pro Ile Glu Lys Thr Ile Ser Lys Ala Lys Gly Gln
        675                 680                 685

Pro Arg Glu Pro Gln Val Tyr Thr Leu Pro Pro Ser Arg Asp Glu Leu
    690                 695                 700

Thr Lys Asn Gln Val Ser Leu Thr Cys Leu Val Lys Gly Phe Tyr Pro
705                 710                 715                 720

Ser Asp Ile Ala Val Glu Trp Glu Ser Asn Gly Gln Pro Glu Asn Asn
                725                 730                 735

Tyr Lys Thr Thr Pro Pro Val Leu Asp Ser Asp Gly Ser Phe Phe Leu
            740                 745                 750

Tyr Ser Lys Leu Thr Val Asp Lys Ser Arg Trp Gln Gln Gly Asn Val
        755                 760                 765

Phe Ser Cys Ser Val Met His Glu Ala Leu His Asn His Tyr Thr Gln
    770                 775                 780

Lys Ser Leu Ser Leu Ser Pro Gly Lys Lys Asp Pro Lys Phe Trp Val
785                 790                 795                 800

Leu Val Val Val Gly Gly Val Leu Ala Cys Tyr Ser Leu Leu Val Thr
                805                 810                 815

Val Ala Phe Ile Ile Phe Trp Val Arg Ser Lys Arg Ser Arg Leu Leu
            820                 825                 830

His Ser Asp Tyr Met Asn Met Thr Pro Arg Arg Pro Gly Pro Thr Arg
        835                 840                 845

Lys His Tyr Gln Ala Tyr Ala Ala Arg Asp Phe Ala Ala Tyr Arg
    850                 855                 860

Ser Leu Arg Val Lys Phe Ser Arg Ser Ala Asp Ala Pro Ala Tyr Gln
865                 870                 875                 880

Gln Gly Gln Asn Gln Leu Tyr Asn Glu Leu Asn Leu Gly Arg Arg Glu
                885                 890                 895

Glu Tyr Asp Val Leu Asp Lys Arg Arg Gly Arg Asp Pro Glu Met Gly
            900                 905                 910

Gly Lys Pro Arg Arg Lys Asn Pro Gln Glu Gly Leu Tyr Asn Glu Leu
        915                 920                 925

Gln Lys Asp Lys Met Ala Glu Ala Tyr Ser Glu Ile Gly Met Lys Gly
    930                 935                 940

Glu Arg Arg Arg Gly Lys Gly His Asp Gly Leu Tyr Gln Gly Leu Ser
945                 950                 955                 960

Thr Ala Thr Lys Asp Thr Tyr Asp Ala Leu His Met Gln Ala Leu Pro
                965                 970                 975

Pro Arg

<210> SEQ ID NO 21

<211> LENGTH: 3006
<212> TYPE: DNA
<213> ORGANISM: artificial
<220> FEATURE:
<223> OTHER INFORMATION: synthetic molecule
<220> FEATURE:
<221> NAME/KEY: CDS
<222> LOCATION: (1)..(2985)

<400> SEQUENCE: 21

```
atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tct aga atg gcc cag gtg caa ctg cag cag tca ggg gct      96
Val Ile Met Ser Arg Met Ala Gln Val Gln Leu Gln Gln Ser Gly Ala
                20                  25                  30 gag ctg gct aga cct ggg gct tca gtg aag atg tcc tgc aag gct tct     144
Glu Leu Ala Arg Pro Gly Ala Ser Val Lys Met Ser Cys Lys Ala Ser
            35                  40                  45 ggc tac acc ttt act acc tac aca ata cac tgg gta aga cgg agg cct     192
Gly Tyr Thr Phe Thr Thr Tyr Thr Ile His Trp Val Arg Arg Arg Pro
        50                  55                  60 gga cac gat ctg gaa tgg att gga tac att aat cct agc agt gga tgt     240
Gly His Asp Leu Glu Trp Ile Gly Tyr Ile Asn Pro Ser Ser Gly Cys
65                  70                  75                  80 tct gac tac aat caa aac ttc aag ggc aag acc aca ttg act gca gac     288
Ser Asp Tyr Asn Gln Asn Phe Lys Gly Lys Thr Thr Leu Thr Ala Asp
                85                  90                  95 aag tcc tcc aac aca gcc tac atg caa ctg aac agc ctg aca tct gag     336
Lys Ser Ser Asn Thr Ala Tyr Met Gln Leu Asn Ser Leu Thr Ser Glu
                100                 105                 110 gac tct gcg gtc tat tac tgt gca aga aga gcg gac tat ggt aac tac     384
Asp Ser Ala Val Tyr Tyr Cys Ala Arg Arg Ala Asp Tyr Gly Asn Tyr
            115                 120                 125 gaa tat acc tgg ttt gct tac tgg ggc caa ggg acc acg gtc acc gtc     432
Glu Tyr Thr Trp Phe Ala Tyr Trp Gly Gln Gly Thr Thr Val Thr Val
        130                 135                 140 tcc tca agt gga ggc ggt tca ggt gga ggt ggc tct ggc ggt ggc gga     480
Ser Ser Ser Gly Gly Gly Ser Gly Gly Gly Gly Ser Gly Gly Gly Gly
145                 150                 155                 160 tcg gtc atc gag ctc act cag tct cca aaa ttc atg tcc aca tca gta     528
Ser Val Ile Glu Leu Thr Gln Ser Pro Lys Phe Met Ser Thr Ser Val
                165                 170                 175 gga gac agg gtc aac gtc acc tac aag gcc agt cag aat gtg ggt act     576
Gly Asp Arg Val Asn Val Thr Tyr Lys Ala Ser Gln Asn Val Gly Thr
                180                 185                 190 aat gta gcc tgg ttt caa caa aaa cca ggg caa tct cct aaa gtt ctg     624
Asn Val Ala Trp Phe Gln Gln Lys Pro Gly Gln Ser Pro Lys Val Leu
            195                 200                 205 att tac tcg gca tct tac cga tac agt gga gtc cct gat cgc ttc aca     672
Ile Tyr Ser Ala Ser Tyr Arg Tyr Ser Gly Val Pro Asp Arg Phe Thr
        210                 215                 220 ggc agt gga tct gga aca gat ttc act ctc acc atc agc aat gtg cag     720
Gly Ser Gly Ser Gly Thr Asp Phe Thr Leu Thr Ile Ser Asn Val Gln
225                 230                 235                 240 tct gaa gac ttg gca gag tat ttc tgt cag caa tat cac acc tat cct     768
Ser Glu Asp Leu Ala Glu Tyr Phe Cys Gln Gln Tyr His Thr Tyr Pro
                245                 250                 255 ctc acg ttc gga ggg ggc acc aag ctg gaa atc aaa cgg gcg gcc gca     816
Leu Thr Phe Gly Gly Gly Thr Lys Leu Glu Ile Lys Arg Ala Ala Ala
                260                 265                 270
```

```
gga ggc ggg ggt tct ggt gga ggc gga agc ggt ggc ggg ggt tca gga       864
Gly Gly Gly Gly Ser Gly Gly Gly Gly Ser Gly Gly Gly Gly Ser Gly
        275                 280                 285 ggc ggg ggt tcc ggt ggt ggc ggc agt ggt ggt ggc ggc agt ggt ggt       912
Gly Gly Gly Ser Gly Gly Gly Gly Ser Gly Gly Gly Gly Ser Gly Gly
        290                 295                 300 ggc ggc agt ggt ggt ggc ggc agt gtc gac ggt gtc cac tcc cag gtg       960
Gly Gly Ser Gly Gly Gly Gly Ser Val Asp Gly Val His Ser Gln Val
305                 310                 315                 320 cag att ttc agc ttc ctg cta atc agt gcc tca gtc ata atg tct aga      1008
Gln Ile Phe Ser Phe Leu Leu Ile Ser Ala Ser Val Ile Met Ser Arg
                325                 330                 335 atg gcc cag gtg aag ctg cag cag tct ggc gct gag ttg gtg aaa cct      1056
Met Ala Gln Val Lys Leu Gln Gln Ser Gly Ala Glu Leu Val Lys Pro
                340                 345                 350 ggg gct tca gtg aag ata tcc tgc aag gct tct ggc tac acc ttc act      1104
Gly Ala Ser Val Lys Ile Ser Cys Lys Ala Ser Gly Tyr Thr Phe Thr
                355                 360                 365 gac cat gct att cac tgg gcg aag cag aag cct gaa cag ggc ctg gaa      1152
Asp His Ala Ile His Trp Ala Lys Gln Lys Pro Glu Gln Gly Leu Glu
370                 375                 380 tgg att gga tat att tct ccc gga aat gat gat att aag tac aat gag      1200
Trp Ile Gly Tyr Ile Ser Pro Gly Asn Asp Asp Ile Lys Tyr Asn Glu
385                 390                 395                 400 aag ttc aag ggc aag gcc aca ctg act gca gac aaa tcc tcc agc act      1248
Lys Phe Lys Gly Lys Ala Thr Leu Thr Ala Asp Lys Ser Ser Ser Thr
                405                 410                 415 gcc tac atg cag ctc aac agc ctg aca tct gag gat tct gca gtg tat      1296
Ala Tyr Met Gln Leu Asn Ser Leu Thr Ser Glu Asp Ser Ala Val Tyr
                420                 425                 430 ttc tgt aaa aga tcg tac tac ggc cac tgg ggc caa ggc acc acg gtc      1344
Phe Cys Lys Arg Ser Tyr Tyr Gly His Trp Gly Gln Gly Thr Thr Val
                435                 440                 445 acc gtc tcc tca ggt gga ggc ggt tca ggc gga ggt ggc tct ggc ggt      1392
Thr Val Ser Ser Gly Gly Gly Gly Ser Gly Gly Gly Gly Ser Gly Gly
        450                 455                 460 ggc gga tcg gac atc gag ctc act cag tct cca gcc tcc tta tct gta      1440
Gly Gly Ser Asp Ile Glu Leu Thr Gln Ser Pro Ala Ser Leu Ser Val
465                 470                 475                 480 tct gtg gga gaa act gtc acc atc aca tgt cga gca agt gag aat att      1488
Ser Val Gly Glu Thr Val Thr Ile Thr Cys Arg Ala Ser Glu Asn Ile
                485                 490                 495 tac agt aat tta gca tgg tac caa cag aaa cag gga aaa tct cct cag      1536
Tyr Ser Asn Leu Ala Trp Tyr Gln Gln Lys Gln Gly Lys Ser Pro Gln
                500                 505                 510 ctc ctg gtc tat gct gca aca aac tta gca gat ggt gtg cca tca agg      1584
Leu Leu Val Tyr Ala Ala Thr Asn Leu Ala Asp Gly Val Pro Ser Arg
                515                 520                 525 ttc agt ggc agt gga tcg ggc aca cag tat tcc ctc aag atc aac agc      1632
Phe Ser Gly Ser Gly Ser Gly Thr Gln Tyr Ser Leu Lys Ile Asn Ser
530                 535                 540 ctg cag tct gaa gat ttt ggg agt tat tac tgt caa cat ttt tgg ggt      1680
Leu Gln Ser Glu Asp Phe Gly Ser Tyr Tyr Cys Gln His Phe Trp Gly
545                 550                 555                 560 act ccg tac acg ttc gga ggg ggg acc aag ctg gag ctg aaa gtg gat      1728
Thr Pro Tyr Thr Phe Gly Gly Gly Thr Lys Leu Glu Leu Lys Val Asp
                565                 570                 575 ccc gcc gag ccc aaa tct cct gac aaa act cac aca tgc cca ccg tgc      1776
Pro Ala Glu Pro Lys Ser Pro Asp Lys Thr His Thr Cys Pro Pro Cys
                580                 585                 590
```

```
cca gca cct cca gtc gcg gga ccg tca gtc ttc ctc ttc ccc cca aaa      1824
Pro Ala Pro Pro Val Ala Gly Pro Ser Val Phe Leu Phe Pro Pro Lys
            595                 600                 605 ccc aag gac acc ctc atg atc gcc cgg acc cct gag gtc aca tgc gtg      1872
Pro Lys Asp Thr Leu Met Ile Ala Arg Thr Pro Glu Val Thr Cys Val
    610                 615                 620 gtg gtg gac gtg agc cac gaa gac cct gag gtc aag ttc aac tgg tac      1920
Val Val Asp Val Ser His Glu Asp Pro Glu Val Lys Phe Asn Trp Tyr
625                 630                 635                 640 gtg gac ggc gtg gag gtg cat aat gcc aag aca aag ccg cgg gag gag      1968
Val Asp Gly Val Glu Val His Asn Ala Lys Thr Lys Pro Arg Glu Glu
                645                 650                 655 cag tac aac agc acg tac cgt gtg gtc agc gtc ctc acc gtc ctg cac      2016
Gln Tyr Asn Ser Thr Tyr Arg Val Val Ser Val Leu Thr Val Leu His
            660                 665                 670 cag gac tgg ctg aat ggc aag gag tac aag tgc aag gtc tcc aac aaa      2064
Gln Asp Trp Leu Asn Gly Lys Glu Tyr Lys Cys Lys Val Ser Asn Lys
    675                 680                 685 gcc ctc cca gcc ccc atc gag aaa acc atc tcc aaa gcc aaa ggg cag      2112
Ala Leu Pro Ala Pro Ile Glu Lys Thr Ile Ser Lys Ala Lys Gly Gln
690                 695                 700 ccc cga gaa cca cag gtg tac acc ctg ccc cca tcc cgg gat gag ctg      2160
Pro Arg Glu Pro Gln Val Tyr Thr Leu Pro Pro Ser Arg Asp Glu Leu
705                 710                 715                 720 acc aag aac cag gtc agc ctg acc tgc ctg gtc aaa ggc ttc tat ccc      2208
Thr Lys Asn Gln Val Ser Leu Thr Cys Leu Val Lys Gly Phe Tyr Pro
                725                 730                 735 agc gac atc gcc gtg gag tgg gag agc aat ggg cag ccg gag aac aac      2256
Ser Asp Ile Ala Val Glu Trp Glu Ser Asn Gly Gln Pro Glu Asn Asn
            740                 745                 750 tac aag acc acg cct ccc gtg ctg gac tcc gac ggc tcc ttc ttc ctc      2304
Tyr Lys Thr Thr Pro Pro Val Leu Asp Ser Asp Gly Ser Phe Phe Leu
    755                 760                 765 tac agc aag ctc acc gtg gac aag agc agg tgg cag cag ggg aac gtc      2352
Tyr Ser Lys Leu Thr Val Asp Lys Ser Arg Trp Gln Gln Gly Asn Val
770                 775                 780 ttc tca tgc tcc gtg atg cat gag gct ctg cac aac cac tac acg cag      2400
Phe Ser Cys Ser Val Met His Glu Ala Leu His Asn His Tyr Thr Gln
785                 790                 795                 800 aag agc ctc tcc ctg tct ccg ggt aaa aaa gat ccc aaa ttt tgg gtg      2448
Lys Ser Leu Ser Leu Ser Pro Gly Lys Lys Asp Pro Lys Phe Trp Val
                805                 810                 815 ctg gtg gtg gtt ggt gga gtc ctg gct tgc tat agc ttg cta gta aca      2496
Leu Val Val Val Gly Gly Val Leu Ala Cys Tyr Ser Leu Leu Val Thr
            820                 825                 830 gtg gcc ttt att att ttc tgg gtg agg agt aag agg agc agg ctc ctg      2544
Val Ala Phe Ile Ile Phe Trp Val Arg Ser Lys Arg Ser Arg Leu Leu
    835                 840                 845 cac agt gac tac atg aac atg act ccc cgc cgc ccc ggg ccc acc cgc      2592
His Ser Asp Tyr Met Asn Met Thr Pro Arg Arg Pro Gly Pro Thr Arg
850                 855                 860 aag cat tac cag gcc tat gcc gcc gca cgc gac ttc gca gcc tat cgc      2640
Lys His Tyr Gln Ala Tyr Ala Ala Ala Arg Asp Phe Ala Ala Tyr Arg
865                 870                 875                 880 tcc ctg aga gtg aag ttc agc agg agc gca gac gcc ccc gcg tac cag      2688
Ser Leu Arg Val Lys Phe Ser Arg Ser Ala Asp Ala Pro Ala Tyr Gln
                885                 890                 895 cag ggc cag aac cag ctc tat aac gag ctc aat cta gga cga aga gag      2736
Gln Gly Gln Asn Gln Leu Tyr Asn Glu Leu Asn Leu Gly Arg Arg Glu
```

-continued

```
                  900                 905                 910
gag tac gat gtt ttg gac aag aga cgt ggc cgg gac cct gag atg ggg     2784
Glu Tyr Asp Val Leu Asp Lys Arg Arg Gly Arg Asp Pro Glu Met Gly
        915                 920                 925 gga aag ccg aga agg aag aac cct cag gaa ggc ctg tac aat gaa ctg     2832
Gly Lys Pro Arg Arg Lys Asn Pro Gln Glu Gly Leu Tyr Asn Glu Leu
930                 935                 940 cag aaa gat aag atg gcg gag gcc tac agt gag att ggg atg aaa ggc     2880
Gln Lys Asp Lys Met Ala Glu Ala Tyr Ser Glu Ile Gly Met Lys Gly
945                 950                 955                 960 gag cgc cgg agg ggc aag ggg cac gat ggc ctt tac cag ggt ctc agt     2928
Glu Arg Arg Arg Gly Lys Gly His Asp Gly Leu Tyr Gln Gly Leu Ser
                965                 970                 975 aca gcc acc aag gac acc tac gac gcc ctt cac atg cag gcc ctg ccc     2976
Thr Ala Thr Lys Asp Thr Tyr Asp Ala Leu His Met Gln Ala Leu Pro
            980                 985                 990 cct cgc taa tcctcgagag atccggatta g                                 3006
Pro Arg
```

<210> SEQ ID NO 22
<211> LENGTH: 994
<212> TYPE: PRT
<213> ORGANISM: artificial
<220> FEATURE:
<223> OTHER INFORMATION: Synthetic Construct

<400> SEQUENCE: 22

```
Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Thr Tyr Thr Ile His Trp Val Arg Arg Arg Pro
    50                  55                  60

Gly His Asp Leu Glu Trp Ile Gly Tyr Ile Asn Pro Ser Ser Gly Cys
65                  70                  75                  80

Ser Asp Tyr Asn Gln Asn Phe Lys Gly Lys Thr Thr Leu Thr Ala Asp
                85                  90                  95

Lys Ser Ser Asn Thr Ala Tyr Met Gln Leu Asn Ser Leu Thr Ser Glu
            100                 105                 110

Asp Ser Ala Val Tyr Tyr Cys Ala Arg Arg Ala Asp Tyr Gly Asn Tyr
        115                 120                 125

Glu Tyr Thr Trp Phe Ala Tyr Trp Gly Gln Gly Thr Thr Val Thr Val
    130                 135                 140

Ser Ser Ser Gly Gly Ser Gly Gly Gly Ser Gly Gly Gly
145                 150                 155                 160

Ser Val Ile Glu Leu Thr Gln Ser Pro Lys Phe Met Ser Thr Ser Val
                165                 170                 175

Gly Asp Arg Val Asn Val Thr Tyr Lys Ala Ser Gln Asn Val Gly Thr
            180                 185                 190

Asn Val Ala Trp Phe Gln Gln Lys Pro Gly Gln Ser Pro Lys Val Leu
        195                 200                 205

Ile Tyr Ser Ala Ser Tyr Arg Tyr Ser Gly Val Pro Asp Arg Phe Thr
    210                 215                 220

Gly Ser Gly Ser Gly Thr Asp Phe Thr Leu Thr Ile Ser Asn Val Gln
225                 230                 235                 240
```

-continued

Ser Glu Asp Leu Ala Glu Tyr Phe Cys Gln Gln Tyr His Thr Tyr Pro
              245                 250                 255

Leu Thr Phe Gly Gly Thr Lys Leu Glu Ile Lys Arg Ala Ala Ala
        260                 265                 270

Gly Gly Gly Gly Ser Gly Gly Gly Ser Gly Gly Gly Ser Gly
        275                 280                 285

Gly Gly Gly Ser Gly Gly Gly Ser Gly Gly Gly Ser Gly Gly
        290                 295                 300

Gly Gly Ser Gly Gly Gly Ser Val Asp Gly Val His Ser Gln Val
305                 310                 315                 320

Gln Ile Phe Ser Phe Leu Leu Ile Ser Ala Ser Val Ile Met Ser Arg
              325                 330                 335

Met Ala Gln Val Lys Leu Gln Gln Ser Gly Ala Glu Leu Val Lys Pro
              340                 345                 350

Gly Ala Ser Val Lys Ile Ser Cys Lys Ala Ser Gly Tyr Thr Phe Thr
              355                 360                 365

Asp His Ala Ile His Trp Ala Lys Gln Lys Pro Glu Gln Gly Leu Glu
              370                 375                 380

Trp Ile Gly Tyr Ile Ser Pro Gly Asn Asp Asp Ile Lys Tyr Asn Glu
385                 390                 395                 400

Lys Phe Lys Gly Lys Ala Thr Leu Thr Ala Asp Lys Ser Ser Ser Thr
              405                 410                 415

Ala Tyr Met Gln Leu Asn Ser Leu Thr Ser Glu Asp Ser Ala Val Tyr
              420                 425                 430

Phe Cys Lys Arg Ser Tyr Tyr Gly His Trp Gly Gln Gly Thr Thr Val
              435                 440                 445

Thr Val Ser Ser Gly Gly Gly Gly Ser Gly Gly Gly Gly Ser Gly Gly
              450                 455                 460

Gly Gly Ser Asp Ile Glu Leu Thr Gln Ser Pro Ala Ser Leu Ser Val
465                 470                 475                 480

Ser Val Gly Glu Thr Val Thr Ile Thr Cys Arg Ala Ser Glu Asn Ile
              485                 490                 495

Tyr Ser Asn Leu Ala Trp Tyr Gln Gln Lys Gly Lys Ser Pro Gln
              500                 505                 510

Leu Leu Val Tyr Ala Ala Thr Asn Leu Ala Asp Gly Val Pro Ser Arg
              515                 520                 525

Phe Ser Gly Ser Gly Ser Gly Thr Gln Tyr Ser Leu Lys Ile Asn Ser
530                 535                 540

Leu Gln Ser Glu Asp Phe Gly Ser Tyr Tyr Cys Gln His Phe Trp Gly
545                 550                 555                 560

Thr Pro Tyr Thr Phe Gly Gly Gly Thr Lys Leu Glu Leu Lys Val Asp
              565                 570                 575

Pro Ala Glu Pro Lys Ser Pro Asp Lys Thr His Thr Cys Pro Pro Cys
              580                 585                 590

Pro Ala Pro Pro Val Ala Gly Pro Ser Val Phe Leu Phe Pro Pro Lys
              595                 600                 605

Pro Lys Asp Thr Leu Met Ile Ala Arg Thr Pro Glu Val Thr Cys Val
              610                 615                 620

Val Val Asp Val Ser His Glu Asp Pro Glu Val Lys Phe Asn Trp Tyr
625                 630                 635                 640

Val Asp Gly Val Glu Val His Asn Ala Lys Thr Lys Pro Arg Glu Glu
              645                 650                 655

-continued

```
Gln Tyr Asn Ser Thr Tyr Arg Val Val Ser Val Leu Thr Val Leu His
            660                 665                 670

Gln Asp Trp Leu Asn Gly Lys Glu Tyr Lys Cys Lys Val Ser Asn Lys
            675                 680                 685

Ala Leu Pro Ala Pro Ile Glu Lys Thr Ile Ser Lys Ala Lys Gly Gln
            690                 695                 700

Pro Arg Glu Pro Gln Val Tyr Thr Leu Pro Pro Ser Arg Asp Glu Leu
705                 710                 715                 720

Thr Lys Asn Gln Val Ser Leu Thr Cys Leu Val Lys Gly Phe Tyr Pro
            725                 730                 735

Ser Asp Ile Ala Val Glu Trp Glu Ser Asn Gly Gln Pro Glu Asn Asn
            740                 745                 750

Tyr Lys Thr Thr Pro Pro Val Leu Asp Ser Asp Gly Ser Phe Phe Leu
            755                 760                 765

Tyr Ser Lys Leu Thr Val Asp Lys Ser Arg Trp Gln Gln Gly Asn Val
            770                 775                 780

Phe Ser Cys Ser Val Met His Glu Ala Leu His Asn His Tyr Thr Gln
785                 790                 795                 800

Lys Ser Leu Ser Leu Ser Pro Gly Lys Lys Asp Pro Lys Phe Trp Val
            805                 810                 815

Leu Val Val Val Gly Gly Val Leu Ala Cys Tyr Ser Leu Leu Val Thr
            820                 825                 830

Val Ala Phe Ile Ile Phe Trp Val Arg Ser Lys Arg Ser Arg Leu Leu
            835                 840                 845

His Ser Asp Tyr Met Asn Met Thr Pro Arg Arg Pro Gly Pro Thr Arg
850                 855                 860

Lys His Tyr Gln Ala Tyr Ala Ala Arg Asp Phe Ala Ala Tyr Arg
865                 870                 875                 880

Ser Leu Arg Val Lys Phe Ser Arg Ser Ala Asp Ala Pro Ala Tyr Gln
            885                 890                 895

Gln Gly Gln Asn Gln Leu Tyr Asn Glu Leu Asn Leu Gly Arg Arg Glu
            900                 905                 910

Glu Tyr Asp Val Leu Asp Lys Arg Arg Gly Arg Asp Pro Glu Met Gly
            915                 920                 925

Gly Lys Pro Arg Arg Lys Asn Pro Gln Glu Gly Leu Tyr Asn Glu Leu
            930                 935                 940

Gln Lys Asp Lys Met Ala Glu Ala Tyr Ser Glu Ile Gly Met Lys Gly
945                 950                 955                 960

Glu Arg Arg Arg Gly Lys Gly His Asp Gly Leu Tyr Gln Gly Leu Ser
            965                 970                 975

Thr Ala Thr Lys Asp Thr Tyr Asp Ala Leu His Met Gln Ala Leu Pro
            980                 985                 990

Pro Arg
```

CHIMERIC ANTIGEN RECEPTOR AND ITS USE

In a first aspect, the present invention relates to a recombinant polypeptide containing a domain comprising at least two antibody units whereby one antibody unit is an anti-CD30 single chain antibody unit while another antibody unit is an antibody unit being specific for an antigen present on the surface of a predetermined target cell. In particular, the present invention relates to a recombinant polypeptide containing at least the following domains starting from the N-terminus to the C-terminus: a first domain containing an anti-CD30 single chain antibody unit, in particular, HRS3 scFv of SEQ ID No. 2 or homologous thereof having at least 70% identity with SEQ ID No. 2 binding specifically to CD30, and an antibody unit said antibody unit being specific for an antigen present on the surface of a predetermined target cell, in particular, being specific for a tumor-associated antigen; optionally a spacer domain; a trans-membrane domain; and a cytoplasmatic signalling domain. The recombinant polypeptide can likewise be arranged in the order where the domain comprising at least two antibody units has the order: a first domain containing an antibody unit specific for a tumor-associated antigen and the second domain containing an anti-CD30 single chain antibody unit. In a further aspect, the present invention relates to a nucleic acid molecule encoding the polypeptide according to the present invention, as well as vectors and cells containing the same. Moreover, lymphocytes are provided, in particular T-cells like $CD8^+$ or a $CD4^+$ T-cell, expressing on its surface chimeric antigen receptors containing an anti-CD30 single chain antibody unit and an antibody unit whereby said antibody unit being specific for an antigen present on the surface of a predetermined target cell.

These cells are particularly useful in treating cancer, in particular $CD30^-$ cancer. That is, the cells are for use in adoptive cell therapy for treating cancer in a subject in need thereof.

PRIOR ART

Adoptive T-cell transfer has shown significant efficacy in the treatment of malignancies and can be curative in patients with various diseases including leukaemia or Epstein Barr virus associated malignancies. Usually, patient derived T-cells are engineered ex vivo to express a recombinant T-cell receptor or, alternatively, a Chimeric Antigen Receptor. Said Chimeric Antigen Receptor (CAR) is typically composed of an extracellular antigen binding domain derived from an antibody and an intracellular T-cell activation domain derived from the T-cell receptor endodomain. In contrast to the physiological TCR, the CAR is composed of one single polypeptide chain that combines antigen binding via the extracellular moiety with a T-cell activation machinery provided by the intracellular signalling moiety. Thus, due to the antibody derived binding domain, CAR modified T-cells recognize their target, usually, a cell surface antigen, independently of the Major Histocompatibility Complex (MHC) presentation of antigen and are not compromised by tumour cell variants with lowered or deficient antigen possessing which represents a commonly observed mechanism of tumour immune escape. CARs are in the focus of research in the recent years. In particular, their capacity to target and lyse pre-defined cells are in the focus of immunotherapy. Recent clinical trials have underscored the potential of adaptive therapy of cancer with CAR-redirected T-cells. For example, neuroblastoma patients treated with GD2 Ganglioside-specific CAR T-cells showed some encouraging anti-tumour effects although the T-cells persist only for a brief period. Further studies proved the concept that CAR engineered T-cells can initiate a productive anti-tumour response in patients suffering from various malignancies. The CAR approach differs to other antibody mediated immune therapy strategies, e.g. by using immunotoxins, in so far that engineered cells are used instead of single molecules.

In recent years, efforts have been done in the optimization of the CAR design, see e.g. Bridgeman J. S., et al., Curr Gene Ther 2010, 10, 77-90. However, many challenges remain, in particular, the necessity of a more effected anti-tumour response and prolonging T-cell survival allowing long term T-cell persistence of said engineered T-cells in the body. In addition, the co-stimulatory signals required for a successful clinical application remains to be illusive, e.g. see Hombach A, et al., Curr Mol Med. 2013 August; 13(7):1079-88. Hence, there is ongoing work on optimizing CAR for various approaches including adaptive immunotherapy.

Hombach A., et al., Gene Therapy, 2010, 17, 1206-1213 describe the modification of the IgG1 Fc spacer domain in the extracellular moiety of Chimeric Antigen Receptors for avoiding off-target activation and unintended initiation of an innate immune response. Therein, T-cells engineered with modified CAR, either an anti-CD30 CAR or an anti-CEA CAR, have been used. As demonstrated therein, anti-CEA CAR T-cells are not effective against CEA negative cells and anti-CD30 CAR T-cells not against $CD30^-$ cells. The modification disclosed in this publication relates to the avoidance of target activation by unintended initiation of the immune response, e.g. due to cross reactivity with a spacer domain in the extracellular moiety of the CAR.

In Kofler et al., 2011, Mol. Ther. 19, 760-767 a CAR molecule is described having a CD28 endodomain combined with a CD3 endodomain and an antibody derived scFv ectodomain specific for CEA. It is described therein, that a deletion of the lck binding moiety in the CD28 CAR endodomain improves redirected anti-tumour activity in presence of T-regulatory cells without impairment of interferon-gamma secretion, proliferation and cytolysis. It is speculated, that the CAR with the modified CD28 endodomain expedite the implementation of adoptive T-cell therapy in patients with a variety of cancer types that are heavily infiltrated by regulatory T-cells (Treg cells).

A summary of the present knowledge on chimeric antigen receptor redirected T-cells is given in the review article of Chmielewski M., et al, frontiers in immunology, 2013, 4, 1-7 as well as in Melenhorst J J, Levine B L., Cytotherapy. 2013 September; 15(9):1046-53. In addition, a summary of adoptive therapy of cancer with CAR redirected T-cells is provided in Hombach A., et al., Curr Mol Med, 2013, 13(1), 1-10. Therein, the effects of CAR are summarized including co-stimulation activity as well as improvement and prolongation of the redirected anti-tumour T-cell response. In addition, the adverse effects of this kind of adaptive therapy are described including "cytokine storm" and "T-cell repression".

Recently, Chmielewski et al, Immunol Reviews vol. 257, 2014, p83-90 discusses the possibility of CAR T-cells engineered with an inducible cytokine to modulate the tumor stroma.

Wilkie, S. et al., J. Clin. Immunol., 2012, 32, 1059-1070 describe a dual targeting of ErB2 and MUC1 in breast cancer using two separate CARs, each capable for full T cell activation. Kloss et al., Nat Biotechnol. 2013 January; 31(1):71-5, report T cells engineered with two separate CARs which provide complementary signalling. The vectors described therein encode two separate CAR molecules expressed simultaneously by the same T cells.

Grada, Z. et al., Molecular Therapy-Nucleic Acids, 2013, vol. 2, page 105 relate to TanCAR, a novel bispecific CAR for cancer immunotherapy. The CAR molecules described therein are designed to identify ligands both being present on the target cell.

That is, currently used chimeric antigen receptor (CAR) modified T-cells for antigen-redirected targeting towards tumor cells show insufficient performance in the anti-tumor attack due to various reasons, in particular due to less amplification and cytolytic activity after adoptive transfer into the patient. Hence, a major obstacle of the strategy for clinical use is the insufficient performance of engineered T-cells in the long-term.

Further, beside beneficial effect of the CAR expressing T-cell in adoptive therapy, ample effects are known which presently hinder favourite development of respective therapy as mentioned above.

BRIEF DESCRIPTION OF THE PRESENT INVENTION

The present invention aims at improving persistence and performance of CAR T-cells.

In a first aspect, the present invention relates to a recombinant polypeptide containing at least the following domains starting from the N-terminus to the C-terminus: a first domain containing an anti-CD30 single chain antibody unit, in particular, HRS3 scFv of SEQ ID No. 2 or homologs thereof having at least 70% identity with SEQ ID No. 2 binding specifically to CD30, and an antibody unit said antibody unit being specific for an antigen present on the surface of a predetermined target cell, in particular, being specific for a tumor-associated antigen; optionally a spacer domain; a trans-membrane domain; and a cytoplasmatic signalling domain. In particular, the present invention relates to a recombinant peptide wherein the first domain comprises the anti-CD30 single chain antibody unit in combination with an antibody unit whereby this antibody unit is specific for a tumor-associated antigen. In a favourable embodiment, the anti-CD30 single chain antibody unit is the HRS3 scFv of SEQ ID No. 2 while the antibody unit is a unit binding to the tumor-associated antigen of carcinoembryonic antigen (CEA), in particular of SEQ ID No. 4. In a further aspect, the present invention relates to a nucleic acid molecule encoding the polypeptide according to the present invention as well as a vector comprising said nucleic acid sequence. Moreover, a cell, cell line or host cell containing said nucleic acid sequence or said vector is provided.

In addition, the present invention is directed to a lymphocyte, in particular, a T-cell, like a CD8$^+$ and/or a CD4$^+$ T-cell, expressing on its surface chimeric antigen receptors having in their extracellular domain two antibody units, an antibody unit being specific for an antigen present on the surface of a predetermined target cell, and an anti-CD30 single chain antibody unit. These units are either present in a single polypeptide as defined herein or present in different functional chimeric antigen receptors. These cells are particularly useful for treating tumor cells expressing the antigen on its surface but may not express CD30 on its surface. That is, by combining these two units, namely, the anti-CD30 single chain antibody unit and an antibody domain being specific for a tumor-associated antigen, tumor cells expressing the tumor specific antigen on its surface but being CD30$^-$ can be treated more efficiently. Hence, the present invention provides in a further aspect a method for treating subjects being afflicted with cancer whereby the tumor cells of said cancer express the antigen but are CD30$^-$ (CD30 negative).

In particular, the cells useful for adoptive cell therapy according to present invention express on its surface chimeric antigen receptors having in the extracellular domain the antibody unit being specific for an antigen present on the surface of a predetermined cell, in particular, wherein the antibody unit is an antibody unit being specific for a tumor-associated antigen, and an anti-CD30 single chain antibody unit whereby these two units may be present either in a single polypeptide representing a CAR or may be present in different functional chimeric antigen receptors.

T-cells with the anti-CEA CAR or anti-CD30 CAR released IFN-gamma only upon co-incubation with $CEA^+$ or $CD30^+$ cells, respectively.

Figure 2:
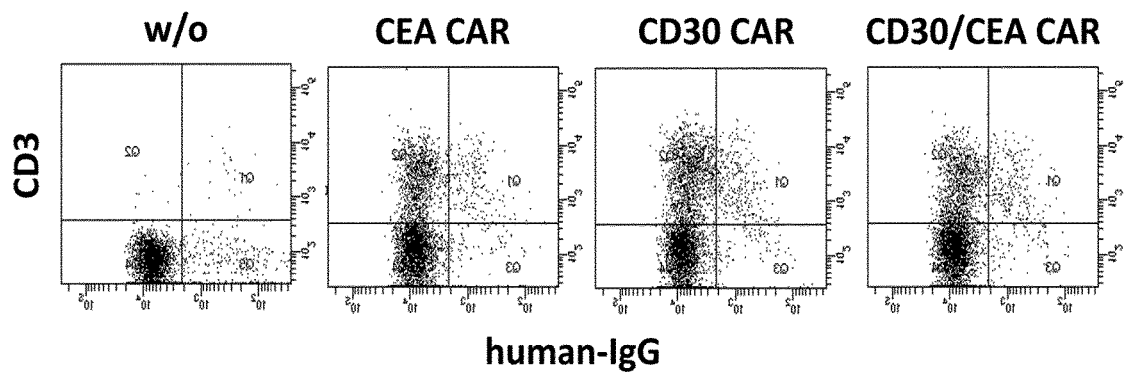
FIG. 2: Peripheral blood lymphocytes were engineered with CARs by standard procedures. After cultivation CD3$^+$ cells where analysed for CAR expression utilising FITC-conjugated anti-CD3 and PE-conjugated anti-human IgG1 Fc antibodies. As demonstrated, transduction was successfully conducted and T-cells express the anti-CD30/CEA CAR on the cell surface in similar amounts as T-cells transduced with the anti-CD30 and anti-CEA CAR, respectively.
Figure 6:
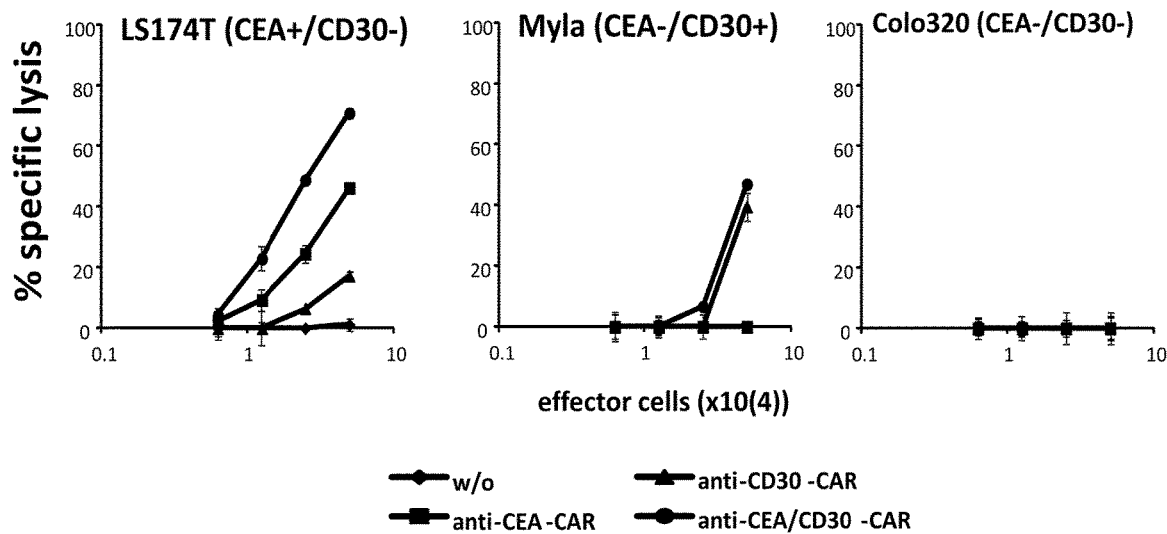

FIG. 6: FIG. 6 shows the cytolytic activity of CAR CIK T-cells (cytokine induced killer cells with NKT-cell phenotype). It is demonstrated that enhanced killing of $CEA^+$ $CD30^-$ target cells by using the anti-CEA/CD30 CAR CIK T-cells is achieved. The tumor cell lines are the same as described in FIG. 2.

Figure 7:
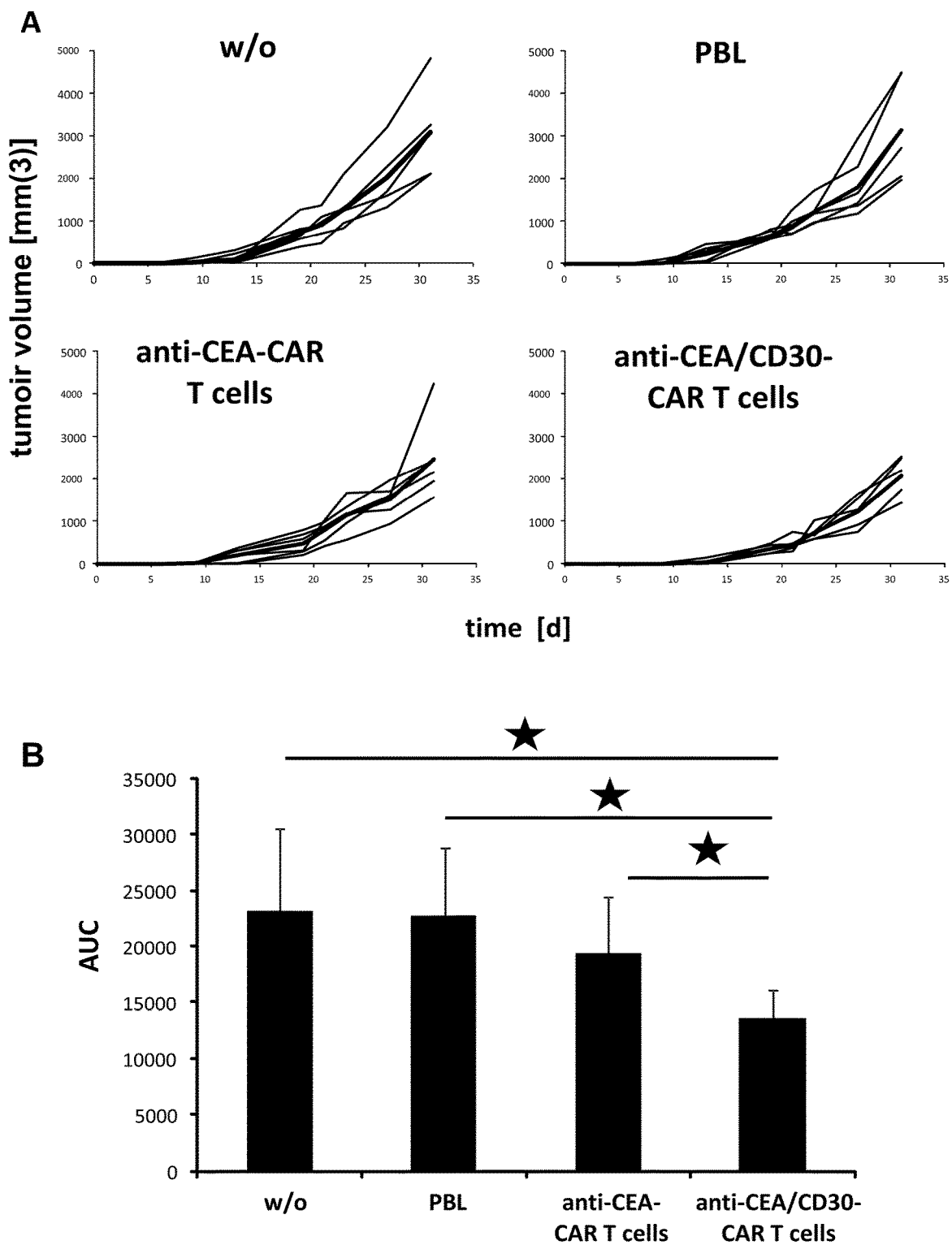

FIG. 7: FIG. 7 demonstrates improved in vivo killing of $CEA^+$ tumor cells by anti-CEA/CD30 CAR T-cells compared to the mono-specific anti-CEA CAR T-cells. Subtherapeutic doses of T-cells ($2.5 \times 10^5$ cells/mouse) without CAR and T-cells engineered either with the anti-CEA/CD30 CAR or the anti-CEA CAR were co-injected with $CEA^+$ $CD30^-$ C15A3 tumor cells ($1 \times 10^6$ cells/mouse) into immune deficient $Rag^{-/-}$ common gamma chain$^{-/-}$ mice. For comparison, C15A3 tumor cells were injected without T-cells (w/o). Tumor volumes and area under curve (AUC) were determined. Significance was determined by Student's T-test. Significant differences ($p<0.05$) were indicated by asterisks.

Figure 8:
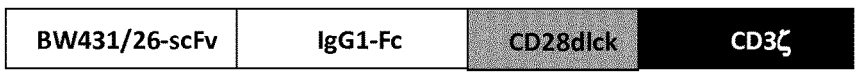
Figure 8:
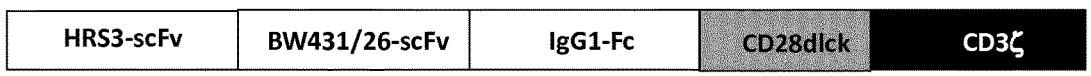
Figure 8:
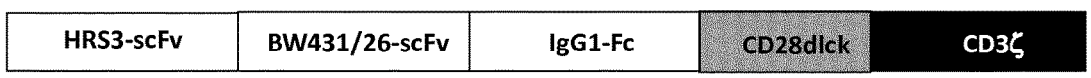
Figure 8:
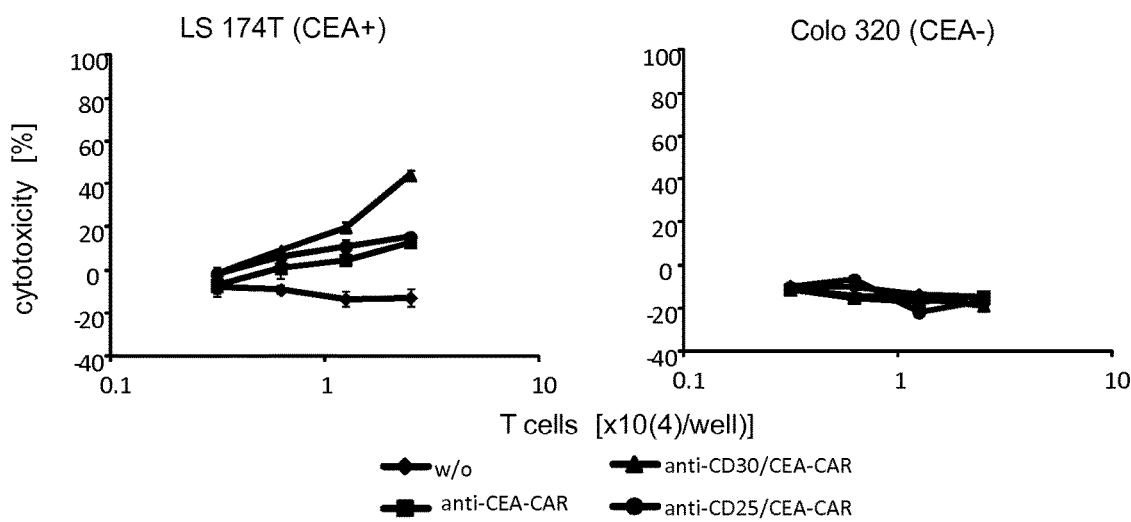

FIG. 8: FIG. 8A shows schematic representation of anti-CD30 CARs and the CD25/CEA bispecific CAR of Seq. ID. No. 18 encoded by the sequence of Seq. ID. No. 17. The HRS3-scFv of CAR #1457 was exchanged by the anti-CD25-scFv RFT5. The backbone of the resulting #1576 CAR is identical to CAR #1457 shown in FIG. 1.

FIG. 8B shows the specificity of cytotoxicity. CAR T cells ($0.625-5 \times 10^4$ cells/well) where co-incubated for 24 hours with CEA+ or CEA− tumor cells ($2.5-5 \times 10^4$ cells/well) as indicated. Only CAR T cells expressing the bispecific anti-CD30/CEA CAR lysed CEA+ target cells whereas CAR T cells with the bispecific anti-CD25/CEA CAR and CAR T cells with a monospecific anti CEA CAR lysed CEA+ targets with lower efficiency. CEA-tumor cells were not lysed demonstrating the CEA-specificity of CAR T cells.

Figure 9:
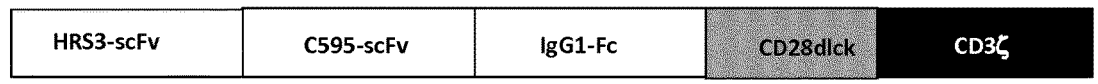
Figure 9:
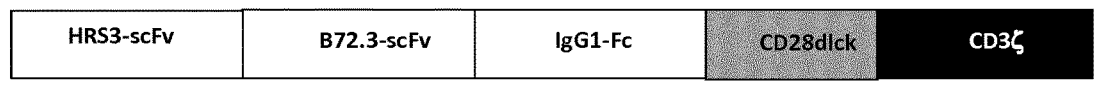
Figure 9:
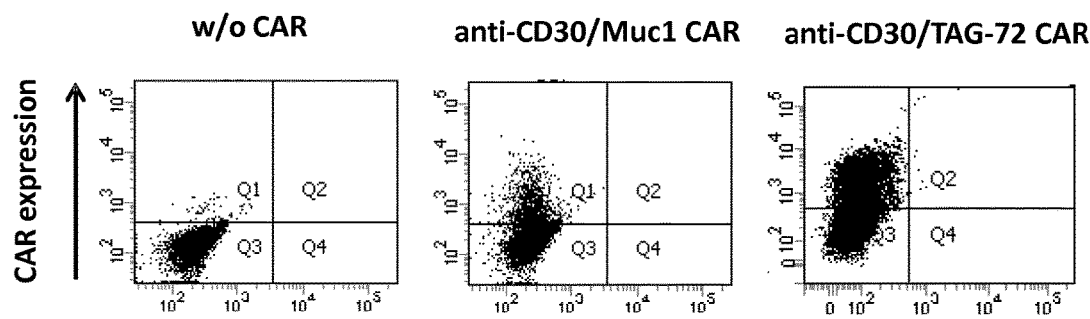

FIG. 9: FIG. 9A is a schematic representation of the molecular composition of the CAR molecules with specificity for CD30/MUC1 of Seq. ID. No. 20 encoded by the sequence of Seq. ID. No. 19 and CD30/TAG-72 of Seq. ID. No. 22 encoded by the sequence of Seq. ID. No. 21. B72.3 is used for the anti-TAG-72 CAR. Except for the anti-CEA scFv, the molecules are identical with the CAR shown in FIG. 1. Cells surface expression of CD30/Muc1 and CD30/ TAG-72 CARs is demonstrated in FIG. 9B by flow cytometry.

DETAILED DESCRIPTION OF THE PRESENT INVENTION

The inventors aim to provide new recombinant polypeptides containing at least the following domains starting from the N-terminus to the C-terminus: a first domain containing an anti-CD30 single chain antibody unit, in particular, HRS3 scFv of SEQ ID No. 2 or homologous thereof having at least 70% identity with SEQ ID No. 2 binding specifically to CD30, and an antibody unit said antibody unit being specific for an antigen present on the surface of a predetermined target cell, in particular, being specific for a tumor-associated antigen; optionally a spacer domain; a trans-membrane domain; and a cytoplasmatic signalling domain. These recombinant polypeptides represent bispecific CAR peptides. In an embodiment of the present invention, these CAR polypeptides are expressed by genetically engineered T-cells containing and eventually expressing these CAR polypeptides.

That is, in a further aspect, the present invention relates to a recombinant polypeptide being at least the following domains starting from the N-terminus to the C-terminus: a first domain containing an anti-CD30 single chain antibody unit, in particular, HRS3 scFv of SEQ ID No. 2 or homologous thereof having at least 70% identity with SEQ ID No. 2 binding specifically to CD30, and an antibody unit said antibody unit being specific for an antigen present on the surface of a predetermined target cell, in particular, being specific for a tumor-associated antigen; optionally a spacer domain; a trans-membrane domain; and a cytoplasmatic signalling domain.

The present invention likewise relates to the following domains, a first domain an antibody unit said antibody unit being specific for an antigen present on the surface of a predetermined target cell, and a second domain containing an anti-CD30 single chain antibody unit, optionally a spacer domain; a trans-membrane domain; and a cytoplasmatic signalling domain.

As used herein, the term "comprise" or "comprising" as well as the terms "contain" or "containing" includes the embodiment of "consist" or "consisting".

The term "homolog" as used herein refers to molecules, either DNA or polypeptides, having a sequence homology of a certain amount, namely of at least 70%, like at least 80%, 90%, 95%, 96%, 97%, 98%, 99% of the nucleic acid sequence or the amino acid sequence it is referred to. Homology refers to the magnitude of identity between two sequences. Homolog sequences have the same or similar characteristics, in particular, have the same or similar property of the sequence as identified. For example, the homolog of the HRS3 scFv sequence of Seq. ID. No. 2 has the same or similar binding specificity to the CD30 molecule as it is the case for the HRS3 scFv molecule. Further, homologs include nucleic acid molecules encoding the same peptide but may vary in its sequence due to the degeneracy of the genetic code. Further, "identify" refers to the presence of identical amino acid or nucleic acid molecules in the order as described for the sequence it refers to. That is, in case of at least 90% identity, 90% or more of the nucleic acid and amino acid molecules, respectively, are identical at the respective positions. Unless otherwise identified, the terms "homology" and "identity" are used herein interchangeably. In particular, the homolog of the HRS3 scFv sequence of Seq. ID. No. 2 include anti CD30 single chain antibody units binding to the same epitope recognized by the HRS3 scFv.

In addition, the term "genetically engineered" refers to cells being manipulated by genetic engineering. That is, the cells contain a heterologous sequence which does not naturally occur in said cells. Typically, the heterologous sequence is introduced via a vector system or other means for introducing nucleic acid molecules into cells including liposomes. The heterologous nucleic acid molecule may be integrated into the genome of said cells or may be present extra-chromosomally, e.g. in the form of plasmids. The term also includes embodiments of introducing genetically engineered, isolated CAR polypeptides into the cell.

Generally, CARs are fusion proteins, consisting of an extracellular antibody type recognition domain fused to intracellular T-cell signalling proteins. Typically, the ectodomain containing the antigen recognition region comprises a signal peptide and an antigen recognition unit. According to the present invention, the ectodomain comprises an anti CD30 single chain unit in combination with an antibody unit being specific for an antigen present on the surface of a predetermined target cell, in particular, being specific for a tumor-associated antigen. It is preferred, that said single chain unit is a single chain unit selected from HRS3 scFv of SEQ. ID. No. 2 or homologous thereof having at least 70% identity with SEQ ID No. 2 and binding specifically to CD30. Further, the single chain unit may be derived from other anti-CD30 antibodies like HRS4 or Ki-4. Said antibodies have the same binding specificity to the same epitope of CD30 as it is the case for the HRS3 antibody. That is, in an embodiment of the present invention, it is preferred that the anti-CD30 single chain unit is a single chain unit being specific to the epitope of the CD30 molecule recognized by the anti CD30 single chain unit HRS3 scFv of Seq. ID. No. 2.

The ectodomain may be spaced apart from the transmembrane domain by the presence of a spacer domain. Said optional spacer domain links the antigen-binding domain to the transmembrane domain and it is preferred that said trans-membrane domain is flexible enough to allow the antigen binding domain to orient in different directions to facilitate antigen recognition.

The transmembrane domain is typically a hydrophobic alpha helix that spans the membrane. Finally, the endodomain represents the signalling domain in the cytoplasma of the cells.

Further, the term "antibody unit being specific for an antigen present on the surface of a predetermined target cell" refers to the binding site derived from an antibody of any species either in form of a single polypeptide chain or multiple covalently or non-covalently associated polypeptide chains. These domains are characterized by specific binding to a molecule on the surface of a target cell. Any other binding moiety than an antibody can alternatively be used as targeting domain in a CAR, e.g., the binding moiety of a receptor like a cytokine receptor.

Moreover, the term "antibody unit being specific for a tumor-associated antigen" refers to a binding domain with specificity to a target molecule present on the cell surface expressed by tumor cells and composed of a polypeptide, carbohydrate or lipid or combinations thereof that are exclusively or preferentially expressed by malignant cells.

The term "functional CAR" refers to a CAR expressed by immune cells that by specific binding to the cognate target molecule activates the same immune cell to increase protein biosynthesis, cytokine secretion, cell proliferation and target cell lysis.

Moreover, the term "CD30$^+$ cells" or "CD30$^+$ cancer cells" refers to cells (either non-cancer or cancer cells) expressing on their surface the CD30 molecule.

The terms "non-tumor cells" and "tumor cells" as well as "non-cancer cells" and "cancer cells" are used herein interchangeably unless otherwise defined.

The term "CIK T-cells" or "NK T-cells" which are used herein interchangeably refers to a heterogeneous group of T-cells that share properties of both T-cells and natural killer (NK) cells. CAR CIK T-cells are obtained by known cultivation techniques to obtain firstly NK T-cells or CIK T-cells and, thereafter, engineering the same cells with the CAR by known methods.

The recombinant polypeptide according to the present invention represents a bispecific CAR also identified herein as dual specific CAR. In an embodiment, the order in the first domain is from the N-terminus to the C-terminus: i) an anti-CD30 single chain antibody unit and an antibody unit, said antibody unit being specific for an antigen present on the surface of a predetermined target cell, or ii) an antibody unit whereby said antibody unit being specific for an antigen present on the surface of a predetermined target cell, and an anti-CD30 single chain antibody unit.

It is preferred that the antibody unit being specific for an antigen present on the surface of a predetermined target cell is an antibody unit being specific for a tumor-associated antigen.

In an embodiment of the present invention, the CAR present in the T-cell comprises a leader sequence being located N-terminally to the first domain containing the anti CD30 single chain unit and the antibody unit.

In addition, in another embodiment, the anti-CD30 single chain antibody unit is a HRS3 scFv peptide, in particular, of SEQ. ID. No. 2, e.g. encoded by the nucleic acid sequence of Seq. ID. No. 1. It has been recognized herein that an anti-CD30 single chain antibody fragment of the variable region (scFv), in particular, of HRS3, allows displaying the desired activity. In an embodiment, the anti CD30 single chain antibody fragment is a fragment recognizing and binding to the epitope of HRS scFv.

In another embodiment, the spacer domain of the CAR molecule is an IgG$_1$ hinge-CH2CH3 domain of SEQ. ID. No. 6 or homologs thereof having at least 70% identity therewith, preferably, the spacer domain is a mutated IgG$_1$ hinge-CH2CH3 domain according to SEQ. ID. No. 6, e.g. encoded by the nucleic acid sequence of Seq. ID. No. 5.

In some embodiments, a linker may be located between the spacer domain and the transmembrane domain.

Further, another embodiment relates to a T-cell with a chimeric antigen receptor wherein the transmembrane domain is derived from the CD28 molecule, e.g. the transmembrane domain of the CD28 molecule lacking the lck domain of SEQ. ID. No. 8, e.g. encoded by the nucleic acid sequence of Seq. ID. No. 7.

The signalling domain or endodomain or intracellular domain which are used herein interchangeably, contains a CD3 zeta or FcEpsilon-Receptor gamma chain signalling chain or a co-stimulatory domain or both the CD3zeta and a co-stimulatory domain or the FcEpsilon-Rezeptor gamma chain and a co-stimulatory domain. For example, the intracellular domain is a CD3 zeta signalling domain of SEQ. ID. No. 10, e.g. encoded by the nucleic acid sequence of Seq. ID. No. 9, or a homolog thereof having at least 70% homology. In another embodiment, the intracellular domain is the IgE Fc-Receptor gamma signalling domain of SEQ. ID. No. 12, e.g. encoded by the nucleic acid sequence of Seq. ID. No. 11, or a homolog thereof having at least 70% identity. The signalling domain is responsible for the activation of the T-cells, in particular the cytotoxic activity and cytokine release including Interferon gamma secretion.

The CAR molecule may be a so-called second generation CAR molecule. Second generation CAR molecules have improved signalling domains additionally containing a second signalling (costimulatory) domain, e.g. derived from CD28, CD134 (OX40) or CD137 (4-1BB). Third generation CAR molecules contain a combined co-stimulatory signalling domain, e.g., CD28 combined with CD137 or CD134.

An overview about the CAR molecules is provided e.g. in Gilham D. E. et al., Trans. and Molecular Medicine, 2012, 18(7), 377-384.

In a preferred embodiment of the present invention, the T-cell is a T-cell with a chimeric antigen receptor wherein the chimeric antigen receptor is a polypeptide of SEQ. ID. No. 14, e.g. encoded by the nucleic acid sequence of Seq. ID. No. 13. Said CAR is also referred to herein as #1457.

The anti-CD30 anti-CEA CAR #1457 is expressed on the surface of T-cells and is composed in the extracellular part of the anti-CD30 single chain fragment of variable region (scFv) antibody HRS3, the BW431/26 scFv antibody corresponding to Seq. ID. No. 4, e.g. encoded by the nucleic acid sequence of Seq. ID. No. 3, corresponding to the anti-CEA antibody BW431/26 and the modified human IgG1 CH2CH3 domain as spacer between scFv and the trans-membrane domain. The modification of the IgG1 domain consists of point mutations to convert the wild-type amino acid sequence PELLGGP $X_{13}$ MISRT (Seq. ID. No. 15) to PPVA-GP $X_{13}$ MIART (Seq. ID. No. 16) which reduces unintended binding of the CAR Fc domain to Fc receptors on other cells like innate immune cells which would mediate their activation. The transmembrane and intracellular membrane proximal part of CAR #1457 is derived from human CD28 and is fused to the intracellular part of human CD3zeta. The CD28 sequence is mutated at P560>A560, P563>A563, P564>A564 (Kofler et al., Mol. Ther. 19, 760-767 (2011). Thereby the CD28 binding site for the lck kinase is destroyed with the consequence that activation of the lck signalling pathway and subsequent CAR mediated IL-2 secretion is prevented. Pre-clinical models imply that Treg cell mediated repression of CAR T-cell effector functions is reduced under these conditions.

As an example, the recombinant polypeptide is the polypeptide of SEQ ID No. 14, e.g. encoded by the nucleic acid sequence of Seq. ID. No. 13 correspond to the #1457 CAR shown in FIG. 1.

In another embodiment, the recombinant polypeptide is a polypeptide wherein the antibody unit binds to a tumor-associated antigen including any one of carcinoembryonic antigen (CEA), CA19-9, CA72-4 also known as TAG-72, PSCA, Muc-1, HMW-MAA, p97 melanotransferrin, fetal actelycholin receptor, ErbB2 (Her2/neu), multi-drug-resistance protein (MDR), CD19, CD20, TOSO.

For example, the CAR #1457 of Seq. ID. No. 14 correspond to a polypeptide wherein the antibody unit being specific to CEA. Further, CARs useful according to the present invention are shown in FIG. 9, namely, CD30/MUC-1 CAR or CD30/Tag72 CAR. These CARs are #1587, anti-CD30/MUC1, of Seq. ID. No. 20 encoded by the sequence of Seq. ID. No. 19, and #1650 anti-CD30/TAG-72 of Seq. ID. No. 22 encoded by the sequence of Seq. ID. No. 21.

In another aspect, the antibody unit binds to viral antigens, in particular, hepatitis virus B-associated antigen S or L, cytomegalovirus-associated antigen or other viral antigens described in the art as being useful for detecting and, eventually, destroying virus infected cells.

As demonstrated in the examples, T-cells (either CD4 or CD8 T-cells) or CIK-cells demonstrate specific lysis of cells not expressing CD30 but expressing the antigen to which the antibody unit is specifically binding only. That is, surprisingly the percentage of specific lysis is higher with the bispecific CAR molecule compared to the monospecific molecule containing the antibody binding unit specific for the antigen present on the surface of the predetermined target cell only.

It is preferred, that the target cell is a tumor cell. Further, the target cell may be a virus loaded cell, e.g. a cell infected with a virus.

Moreover, the predetermined target cell may be a cell involved in autoimmune defects in a subject. In that particular case suppressor cells, in particular regulatory T-cells, are modified with the described CAR in order to repress the acute inflammatory immune reaction in the targeted tissue. The CAR binds to tissue antigen with one scFv, e.g., anti-HLA B27, and to CD30 with the other scFv.

Although not expressed by the predetermined target cells, the anti-CD30 single chain antibody unit present in the CAR molecule increases specific lysis of the target cells. Furthermore, it has been surprisingly shown that in case of CD30 negative cells the percentage of specific lysis can be increased as demonstrated in the examples. This is not only true for lysis by CAR expressing T-cells but also by CAR CIK-cells. It is considered that autostimulation of the CAR T-cells allows to increase specific lysis of the target cells.

In addition, the present invention provides nucleic acid molecules comprising the nucleic acid sequence encoding the polypeptide according to the present invention. Furthermore, vectors are provided comprising the nucleic acid sequence according to the present invention encoding the polypeptide as described. The skilled person is well aware of suitable vector systems and vectors, in particular, vectors allowing transfection and transduction of eukaryotic cells, in particular, T-cells.

Moreover, the present invention provides a cell, cell line or a host cell containing the vector according to the present invention or a nucleic acid molecule according to the present invention. Preferably, said cell, cell line or host cell is a T-cell, e.g., a CD4$^+$ T-cell or a CD8$^+$ T-cell.

Further, the present invention provides a kit or system containing the vector according to the present invention, the cell, cell line or host cell according to the present invention, or the polypeptide according to the present invention or a nucleic acid molecule according to the present invention or mixtures thereof for use in the production of T-cells expressing the chimeric antigen receptor. The kit or system according to the present invention may contain further components including means for introducing the vector, polypeptide or nucleic acid molecules into the cells. The skilled person is well aware of suitable means for doing so.

Moreover, the present invention provides lymphocytes, in particular, T-cells, like CD8 and/or CD4 T-cells expressing on its surface chimeric antigen receptors having in the extracellular domain an antibody unit, said antibody unit being specific for an antigen present on the surface for an antigen present on the surface of a predetermined target cell, and an anti-CD30 single chain antibody unit expressed by said cells. The units may be present either in a single polypeptide, e.g. a polypeptide as defined herein, or, alternatively, may be present in different chimeric antigen receptors.

In another aspect, the lymphocyte may be a CAR CIK-T-cell as defined herein.

The lymphocytes including the CD8$^+$, CD4$^+$ or CIK-T-cells demonstrate higher specific lysis of the target cells, thus, reducing side effects and, in addition, overcoming the problem of insufficient performance in the anti-tumor attach due to various reasons, for example, less amplification and cytolytic activity after adopted transfer into the patient.

It is considered that the presence of the anti-CD30 single chain antibody unit allows to amplify the genetically engineered lymphocytes and improve persistence of the same, thus, overcoming the problem of insufficient performance.

The cells are particularly useful in treating cancer, in particular CD30$^-$ cancer whereby said cancer is a cancer expressing on the cancer cells the antigen to which the anti-tumor antigen antibody is directed to.

In a further aspect, the present invention relates to the use of immune cells, e.g. the T-cell with a chimeric antigen receptor according to the present invention in adaptive cell therapy for treating CD30$^-$ or CD30$^+$ cancer in a subject in need thereof. For instance the CD30$^+$ cancer may be Hodgkin's lymphoma, anaplastic large cell lymphoma, acute lymphocytic leukaemia, cutaneous lymphoma, mycosis fungoides, lymphoproliferative diseases, systemic mastocytosis, teratocarcinoma, stem cell derived malignancies, or cancer stem cells or others. In particular the invention relates to the use of such immune cells for the treatment of CD30⁻ cancers, e.g., breast, lung, prostate, pancreas, gastrointestinal carcinomas, neuronal cancer and others. Thus, the present invention may foster adaptive immune therapy by CAR T-cells.

The present invention is further described by way of examples. Said examples illustrate the invention further without limiting the same thereto.

EXAMPLES

Preparation of CAR #1457

Figure 1:
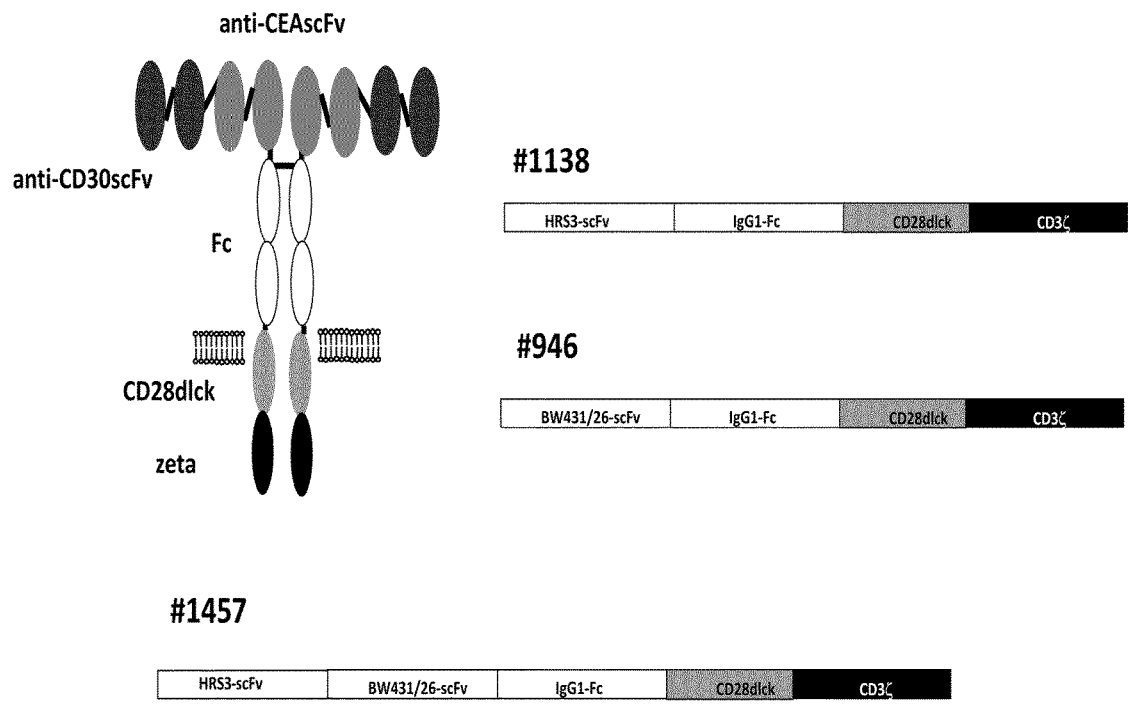
FIG. 1: Schematic representation of the modular composition of the CAR molecules. #1138 represents the anti-CD30 CAR; #946 represents the anti-CEA CAR. The CAR #1457 is the bispecific CAR molecule according to the present invention composed of the anti-CD30 single chain antibody scFv HRS3, the anti-CEA scFv BW431/26, the spacer domain IgG1-Fc, the trans-membrane domain of CD28 and the cytoplasmic signalling domain of the CD28ΔLCK and CD3zeta chain.

The expression cassette of the bispecific anti-CD30/CEA-CAR was generated as follows: The anti-CD30-scFv (HRS3) and the anti-CEA-scFv (BW431/26) were PCR amplified and flanked with a linker by overlapping sequences at the 3'terminus of the CD30-scFv and the 5'terminus of the anti-CEA-scFv while the linker coding for a 40 AA (Gly(4)-Ser(1))5 linker. DNAs of scFvs were assembled by SOE PCR, digested with NcoI and BamHI and ligated into the NcoI/BamHI site of the retroviral vector pBullet-HRS3-scFv-Fc-CD28deltalck-zeta thereby replacing the HRS3-scFv by the combined HRS3-scFv-BW431/26scFv. The resulting vector coding for the bispecific anti-CD30/CEA-CAR was termed #1457. The modular composed #1457 CAR and its mono-specific anti-CEA (#946) and anti-CD30 (#1138) counterparts are schematically shown in FIG. 1.

The retroviral vector coding for the #1457 CAR was produced according to SOP-GL-VectProd using a Galv pseudotyped envelope. In summary vector particle production was done transiently on the human embryonic kidney cell line 293T after Polyfect® mediated DNA transfection. Vector particles were pseudotyped with Galv. No vector titer was determined.

Transduction of human blood lymphocytes was done according to SOP standard techniques. In summary human lymphocytes were transduced with a 2-day supernatant from transfected 293T-cells for 2 days. The CAR #1457 was expressed by 20-35% of human T-cells as measured at day 2 by flow cytometry using an antibody directed to the extracellular constant IgG1 CH2 CH3 domain of the CAR.

CD4⁺ and CD8⁺ T-cells which express the CAR #1457 on the cell surface can be recorded by use of the 9G10 antibody which binds specifically the CAR HRS3 scFv domain. T-cells engineered with the #1457 CAR bind specifically to CD30 expressing cells and become activated indicated by increased secretion of cytokines including IFN-γ, by increase in proliferation and in cytolysis of CD30⁺ target cells. Noteworthy, only background levels of IL-2 are secreted when T-cells are stimulated by the CAR. IL-2, however, is secreted in physiological amounts when T-cells are stimulated by their physiological TCR and CD28. Activation of the T-cells #1457 is antigen-specific as defined by the specificity of the CAR since CD30⁻ cells do not trigger T cell activation. Soluble CD30, which accumulates in the serum of CD30⁺ lymphoma patients, does not block CAR mediated T-cell activation in concentrations up to 10 μg/ml [Hombach A, et al., Cancer Res. 1998 Mar. 15; 58(6):1116-9]. This is due to the fact that the CAR must be cross-linked by binding the multiple copies of the targeted antigen in order to trigger T-cell activation which can only occur when CD30 is immobilized or expressed on the surface of target cells but does not occur when CD30 protein is present in solution.

Example 1: Activity of Dual Specific CAR Modified T-Cells Toward CEA⁺ and/or CD30⁺ Cell Lines Engineering of T-cells with CAR #1457 was performed as described above. The CAR was detected on the T-cell surface by flow cytometry utilizing an antibody against the Fc domain in the extracellular moiety of the CAR (FIG. 1, 2). The anti-CEA/CD30 CAR was expressed with similar efficiency as the mono-specific CARs with either the CD30 or the CEA binding domain. To test for dual specificity of the #1457 CAR, grafted T-cells were co-incubated either with CD30⁺ or CEA⁺ target cells and redirected cytotoxicity and IFN-gamma secretion were monitored. Whereas T-cells with anti-CEA and anti-CD30 CAR were only activated by CEA⁺ or CD30⁺ target cells, respectively, the bispecific CAR activates T-cells after co-culture with both CEA⁺ CD30⁻ and CEA⁻ CD30⁺ tumor cells. T-cell activation results in specific target cell lysis and IFN-gamma secretion (cf. FIG. 4, 5 and Example 3).

Conclusion:

T-cells with the #1457 CAR harbour dual specificity for binding, i.e., for CD30 and CEA. T-cells expressing the bispecific CAR were activated by engaging target cells with one cognate CAR antigen only as well as by target cells with both antigens.

Example 2: Specific Expansion of #1457 CAR Modified T-Cells

Figure 3:
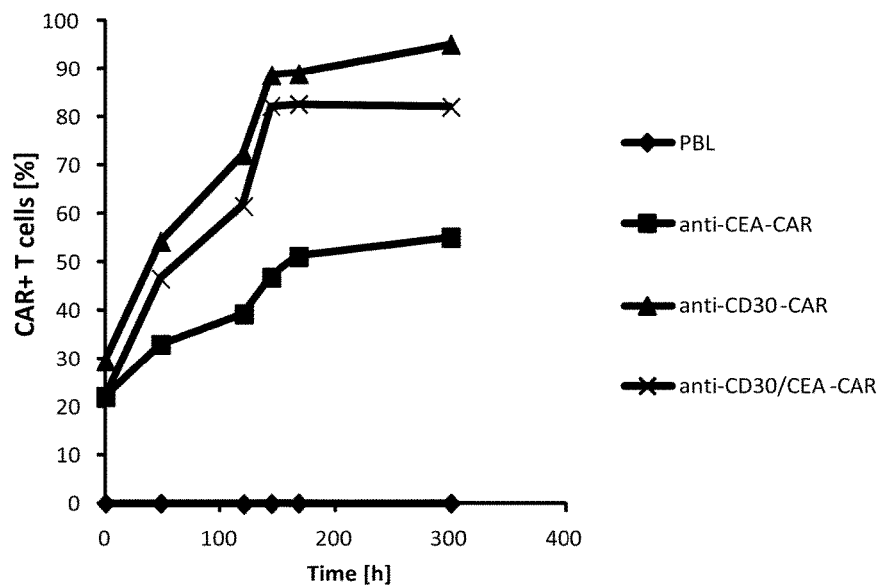
FIG. 3: Human T-cells were engineered with CARs as indicated with an initial CAR expression rate of anti-CEA-CAR: 22.2%; anti-CD30-CAR: 28.9%; anti-CEA/CD30-CAR: 22.8%. CAR T-cells were cultivated 300 hours in the presence of IL-2 and CAR expressing cells were monitored. CAR T-cells with a CD30 binding domain expand more efficiently than T-cell with the anti-CEA CAR only.

T-cells were engineered with the #1457 CAR or for comparison with the corresponding single CD30 or CEA specific CAR, respectively, and cultivated in presence of IL-2 (400 U/ml). The initial number of CAR+ T-cells was 20-30%. Cells were tested at different time points for CAR expression by flow cytometry. As summarized in FIG. 3, the number of T-cells with the anti-CD30-CAR and the anti-CEA/CD30 CAR #1457 increased up to 90% of T-cells during cultivation whereas the number of anti-CEA CAR T-cells did not exceed 50%.

Conclusion

Data demonstrate that CAR T-cells with the CD30-binding domain expand superior compared to CAR T-cells with a CEA binding domain. The superior effect is also present when the anti-CD30 binding domain is linked with the anti-CEA binding domain.

Figure 4:
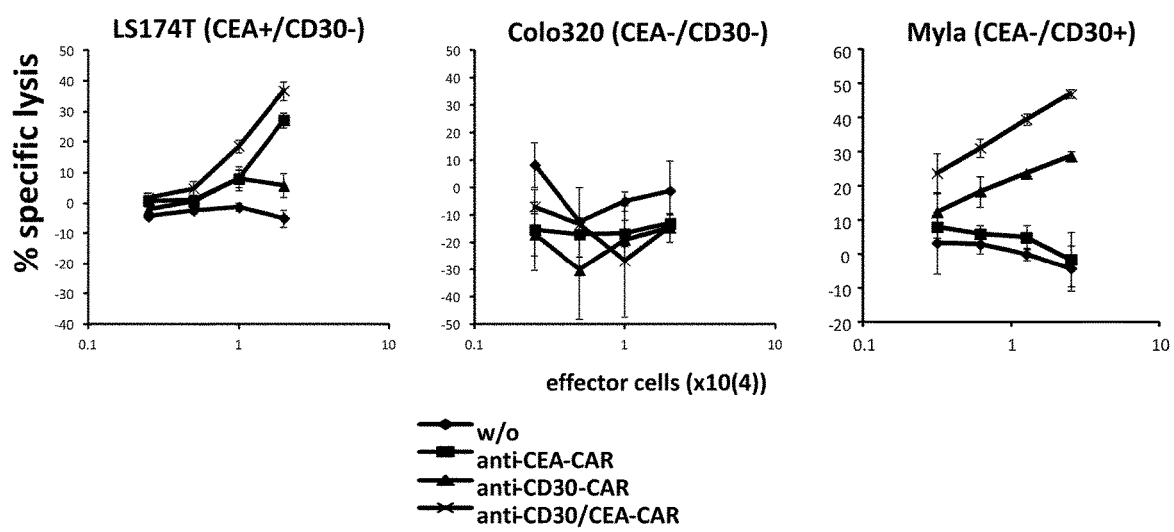
FIG. 4: Engineered human T-cells expressing different kinds of CARs as indicated (initial CAR expression: anti-CEA-CAR: 8.5%; anti-CD30-CAR: 9.3 9%; anti-CEA/CD30-CAR: 8.2%). CAR T-cells (0.625-5×10$^4$ cells/well) where co-incubated for 24 hours with tumor cells (2.5-5×10$^4$ cells/well) as indicated. Three different types of cell lines where used being either positive for CEA or CD30 or as control negative for both CEA and CD30. The cell line being negative for both CEA and CD30 was not lysed while specific lysis of LS174T cells was observed which is a CEA$^+$/CD30$^-$ cell line. Therein, the anti-CEA/CD30 CAR T-cells demonstrate a higher specific lysis compared to the anti-CEA CAR T-cells.

Example 3: Increased Specific Lysis by CAR #1457 Engineered T-Cells and CAR #1457 Engineered CIK T-Cells Toward CD30-Negative Target Cells (a) T-Cells Human T-cells were engineered to express the CAR #1457, the CEA-specific CAR and the CD30-specific CAR, respectively. The same number of CAR T-cells was co-incubated with tumor cells which express either CEA or CD30 or both. Data presented in FIG. 4 show that the cell line being negative for both CEA and CD30 (Colo320) was not lysed while specific lysis of LS174T cells was observed which is a CEA⁺/CD30⁻ cell line. Therein, the anti-CEA/CD30 CAR T-cells demonstrate a higher specific lysis compared to the anti-CEA CAR T-cells.

Figure 5:
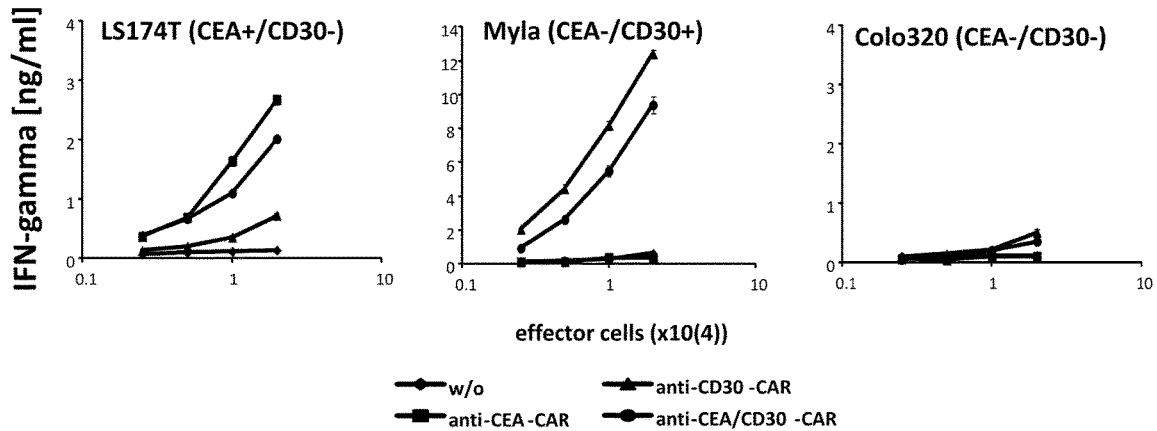
FIG. 5: The release of interferon-gamma, a marker for T-cell activation, during co-cultivation of different numbers of effector cells with the tumor cells is shown. After 24 hours co-cultivation the supernatants were collected and analysed for interferon-gamma by ELISA. The assay was performed in triplicate and the SD was determined. As shown, anti-CEA/CD30 CAR T-cells produced IFN-gamma when co-incubated with the CEA$^+$/CD30$^-$ LS174T-cells as well as with the CEA$^-$ CD30$^+$ cells. No IFN-gamma was produced upon co-incubation with CEA$^-$ CD30$^-$ Colo320 cells.

The cytolytic activity is accompanied by release of IFN-g, a marker for T-cell activation, as shown in FIG. 5. Anti-CEA/CD30 CAR #1457 T-cells produced IFN-gamma when co-incubated with the CEA⁺/CD30⁻ LS174T-cells as well as with the CEA⁻ CD30⁺ cells. No IFN-gamma was produced upon co-incubation with CEA⁻ CD30⁻ Colo320 cells. T-cells with the anti-CEA CAR or anti-CD30 CAR released IFN-gamma only upon co-incubation with CEA⁺ or CD30⁺ cells, respectively.

(b) CIK Cells

CIK cells were generated according to standard procedures and were engineered with the anti-CD30/CEA CAR #1457. After 8 days post transduction #1457 CAR CIK cells were co-cultivated with CD30⁻CEA⁺, CD30⁻CEA⁻ or CD30⁻CEA⁻ target cells and target cell lysis was recorded. CIK cells expressing the corresponding monospecific anti-CD30 and anti-CEA CAR, respectively, served as control. Bispecific anti-CD30/CEA and mono-specific anti-CD30 CAR T-cells lysed CD30⁺ target cells with similar efficiency. In contrast, CAR #1457 CIK cells lysed CEA⁺ CD30⁻ target cells more efficiently than CIK cells with the anti-CEA CAR (FIG. 6). Data indicate that CAR #1457 CIK cells surprisingly show a higher cytolytic activity against tumor cells that do not express CD30 than CIK cells with a CEA-specific CAR.

Conclusion:

T-cells and CIK cells engineered with the CAR #1457 show enhanced anti-tumor reactivity against target cells, both which express and which lack CD30, compared to T-cells with the monospecific CAR. This is unexpected in particular for those target cells which lack CD30.

Example 4: Improved Anti-Tumor Activity of #1457 CAR T-Cells in a Xeno-Graft Mouse Model The in vivo activity of anti-CD30/CEA CAR #1457 T-cells was monitored in the immune deficient Rag⁻/⁻ common gamma chain⁻/⁻ mouse. Anti-CEA-CAR and anti-CD30/CEA CAR #1457 T-cells were engineered as described above and subcutaneously co-injected in a sub-therapeutic dose (2.5×10⁵ CAR T-cells/animal) with CEA⁺ CD30⁻ C15A3 tumor cells (1×10⁶ cells/animal), that were transfected to express human CEA, into mice. Mice without T-cells and non-modified T-cells were used for control and tumor growth was monitored every 2nd-3rd day. Growth curves (FIG. 7A) and area under curve (FIG. 7B) were determined. Whereas anti-CEA-CAR T-cells produced slightly delay of tumor growth, anti-CD30/CEA CAR T-cells significantly delayed tumor growth indicating higher anti-CEA activity of the bispecific CAR T-cells #1457 in vivo than T cells with the anti-CEA CAR.

Conclusion:

Bispecific anti-CD30/CEA CAR T-cells are more effective in an prolonged anti-tumor response against CEA⁺ CD30⁻ tumor cells in vivo compared to T cells with the mono-specific anti-CEA CAR. The improved anti-tumor reactivity is due to the particular CAR design because human CD30 is neither expressed by the murine host nor by the grafted mouse tumor cells and not recognized on tumor cells or on cells of the host.

Example 5: Improved Anti-Tumor Activity of Anti-CD30/CEA #1457 CAR but not Anti-CD25CEA #1576 CAR The bispecific #1576 CAR of Seq. ID. No. 18 encoded by the sequence of Seq. ID. No. 17 with specificity for both the lymphocyte activation antigen CD25 and CEA was generated by substituting the HRS3 scFv with the anti-CD25 scFv RFT5 (FIG. 8A; cf FIG. 1). Engineering of T-cells with CAR #1576 was performed as described above by flanking the cDNA for the anti-CD25 scFv with overlapping sequences and sequences for appropriate restriction enzymes by PCR. The sequence of the HRS3 scFv was substituted and the resulting #1576 CAR expressed by transduction with retroviral supernantant according to transduction SOP. The CAR was detected on the T-cell surface by flow cytometry utilizing an antibody against the Fc domain in the extracellular moiety of the CAR. The anti-CD25/CEA CAR was expressed with similar efficiency than monospecific and bispecific anti-CD30 CARs, respectively. Specific CAR T cell activation and lysis of CEA+ target cells was tested by co-cultivation with CEA+ and CEA− tumor cells respectively. All CARs lysed specifically CEA+ target cells but the anti-CD30/CEA CAR lysed tumor cells with higher efficiency than monospecific and bispecific anti-CEA and anti-CD25/CEA CARs, respectively (FIG. 8B).

Conclusion:

T-cells with the #1457 anti-CD30/CEA CAR but not with the #1576 anti-CD25/CEA CAR were activated against CEA+ target cells with higher efficiency than anti-CEA-monospecific CAR T cells.

Example 6: Bispecific Anti-CD30 Antibodies with Different Second Specificity

Bispecific anti-CD30 CAR molecules were generated as described in Example 1 except for substituting the anti-CEA scFv moiety with scFv moieties with specificity against MUC1, C595-scFv, resulting in anti-CD30/MUC1-CAR #1587, and with specificity against TAG-72, B72.3-scFv, resulting in anti-CD30/TAG-72 CAR #1650. The sequences thereof are Seq. Id. Nos. 20 and 19 for #1587 and Seq. ID. Nos. 22 and 21 for #1650.

FIG. 9A is a schematic representation of these bispecific CARs. FIG. 9B demonstrates expression of these CAR molecules on transfected 293 T-cells.

The invention claimed is:

1. A nucleic acid molecule comprising a nucleic acid sequence encoding a recombinant polypeptide containing at least the following domains starting from the N-terminus to the C-terminus:
   a first domain containing i) an anti-CD30 single chain antibody unit and ii) an antibody unit specific for an antigen present on a surface of a predetermined target cell,
   wherein the target cell is CD30 negative;
   optionally a spacer domain;
   a trans-membrane domain; and
   a cytoplasmatic signalling domain,
   wherein the anti-CD30 single chain antibody unit in the first domain is HRS3 scFv of SEQ ID NO. 2 or homologs thereof having at least 95% identity with SEQ ID NO. 2 binding specifically to CD30.

2. The nucleic acid molecule according to claim 1, wherein said recombinant polypeptide further comprises a leader sequence being located N-terminally to the first domain containing the anti-CD30 single chain antibody unit and the antibody unit specific for the antigen present on the surface of the predetermined target cell being CD30 negative.

3. The nucleic acid molecule according to claim 1, wherein the anti-CD30 single chain antibody unit is the HRS3 scFv peptide of the SEQ ID No. 2.

4. The nucleic acid molecule according to claim 1, wherein the spacer domain is present and is an IgG1 CH2 CH3 domain of SEQ ID No. 6 or homologs thereof having at least 95% identity therewith.

5. The nucleic acid molecule according to claim 1, wherein the trans-membrane domain is obtained from CD28.

6. The nucleic acid molecule according to claim 1, wherein the intracellular domain contains a CD3zeta or a Fc-epsilon receptor I-gamma signalling chain or a costimulatory unit.

7. The nucleic acid molecule according to claim 1, wherein the intracellular domain is a CD28 signalling domain.

8. The nucleic acid molecule according to claim 1, wherein the antibody unit specific for the antigen present on the surface of the predetermined target cell being CD30 negative binds to a tumor-associated antigen selected from the group consisting of carcinoembryonic antigen (CEA), CA19-9, CA72-4 (TAG-72), PSCA, Muc-1, HMW-MAA p97 melanotransferrin, fetal actelycholin receptor, ErbB2 (Her2/neu), multi-drug-resistance protein (MDR), CD19, CD20, and TOSO.

9. The nucleic acid molecule according to claim 1, wherein the antibody unit specific for the predetermined target cell being CD30 negative binds to one or more viral antigens.

10. A vector comprising the nucleic acid sequence according to claim 1.

11. A cell, cell line or host cell containing a nucleic acid molecule according to claim 1 wherein the nucleic acid molecule is isolated, combined with other nucleic acids, or part of a vector.

12. The cell, cell line or host cell according to claim 11 wherein the cell or host cell is a modified peripheral blood cell.

13. The nucleic acid molecule of claim 4, wherein the spacer domain is a mutated IgG1 CH2 CH3 domain according to SEQ ID No. 6.

14. The nucleic acid molecule of claim 6, wherein the intracellular domain is the CD3zeta signalling unit of SEQ ID No. 10 or a homolog thereof having at least 95% homology.

15. The nucleic acid molecule of claim 6, wherein the intracellular domain is the IgE Fc epsilon receptor-I gamma-signalling unit of SEQ ID No. 12 or a homolog thereof having at least 95% homology.

16. The nucleic acid molecule of claim 1, wherein said predetermined target cell is a tumor-associated antigen.

17. The nucleic acid molecule of claim 1 having SEQ ID No. 13.

18. The vector of claim 10, wherein the vector is a viral vector.

19. The cell, cell line or host cell of claim 12, wherein the modified peripheral blood cell is a $CD8^+$ T-cell or a $CD4^+$ T-cell.

20. The nucleic acid molecule of claim 9, wherein the one or more viral antigens are selected from the group consisting of heptatis virus B-associated antigen S or L, and cytomegalovirus-associated antigen.

21. The nucleic acid molecule of claim 7, wherein the CD28 signalling domain lacks the LCK binding motif.

* * * * *